(12) United States Patent
Larsen

(10) Patent No.: US 10,377,778 B2
(45) Date of Patent: Aug. 13, 2019

(54) LEAD AND THORIUM COMPOUNDS

(71) Applicant: Sciencons AS, Oslo (NO)

(72) Inventor: Roy Hartvig Larsen, Oslo (NO)

(73) Assignee: Sciencons AS, Oslo (NO)

( * ) Notice: Subject to any disclaimer, the term of this patent is extended or adjusted under 35 U.S.C. 154(b) by 0 days.

(21) Appl. No.: 16/219,072

(22) Filed: Dec. 13, 2018

(65) Prior Publication Data

US 2019/0177345 A1    Jun. 13, 2019

(30) Foreign Application Priority Data

Dec. 13, 2017 (EP) .................................... 17206887

(51) Int. Cl.

| | |
|---|---|
| *C07F 7/24* | (2006.01) |
| *C07F 3/00* | (2006.01) |
| *C07F 9/94* | (2006.01) |
| *A61P 35/04* | (2006.01) |
| *C07B 59/00* | (2006.01) |
| *A61K 51/04* | (2006.01) |
| *A61P 35/00* | (2006.01) |

(52) U.S. Cl.
CPC ............ *C07F 7/24* (2013.01); *A61K 51/0402* (2013.01); *A61K 51/0497* (2013.01); *A61P 35/00* (2018.01); *A61P 35/04* (2018.01); *C07B 59/002* (2013.01); *C07F 3/003* (2013.01); *C07F 9/94* (2013.01); *C07B 2200/05* (2013.01)

(58) Field of Classification Search
CPC ... A61P 35/04; C07B 59/002; C07B 2200/05; C07F 3/003; C07F 9/94; C07F 7/24; A61K 51/0497; A61K 51/0482; A61K 51/088

See application file for complete search history.

(56) References Cited

U.S. PATENT DOCUMENTS

| | | | |
|---|---|---|---|
| 2013/0034494 A1* | 2/2013 | Babich ................. | C07D 255/02 424/1.65 |
| 2016/0228587 A1* | 8/2016 | Eder ..................... | C07B 59/002 |
| 2016/0250360 A1* | 9/2016 | Larsen ................. | A61K 51/1051 424/1.53 |

FOREIGN PATENT DOCUMENTS

WO    WO 2017/165473    *   9/2017    ........... C07D 257/02

\* cited by examiner

*Primary Examiner* — Michael G. Hartley
*Assistant Examiner* — Leah H Schlientz
(74) *Attorney, Agent, or Firm* — Knobbe, Martens, Olson & Bear LLP

(57) ABSTRACT

The present invention relates complexes comprising a PSMA targeting compound linked to a radionuclide, such as $^{212}$Pb or $^{227}$Th. These compounds, and pharmaceutical compositions comprising them, can be used for medical applications. These applications include the treatment of prostate cancer, and the complexes allow for dual targeting of cancers.

13 Claims, 2 Drawing Sheets

LEAD AND THORIUM COMPOUNDS

CROSS REFERENCE TO RELATED APPLICATION

This application claims the benefit of priority to European Patent Application No. 17206887.6, filed on Dec. 13, 2017, the disclosure of which is hereby expressly incorporated by reference in its entirety

FIELD OF THE INVENTION

The present invention relates to complexes comprising a PSMA targeting compound linked to a radionuclide such as $^{212}$Pb or $^{227}$Th. These compounds, and pharmaceutical compositions comprising them, can be used for medical applications. These applications include the treatment of prostate cancer, and the complexes allow for dual targeting of cancers. Peptide and peptidomimetic PSMA targeting urea derivatives conjugated to chelators for complexing $^{212}$Pb and $^{227}$Th for radiotherapeutic use. These can be used in single and dual targeting.

BACKGROUND OF THE INVENTION

Prostate cancer is among the most frequent causes of cancer related mortality in men. There is a great demand for new and effective treatment, especially in hormone refractory late stage disease. Skeletal metastases are a frequent problem in late stage disease and therefore the alpha-particle emitter $^{223}$Ra (Xofigo) was introduced as a bone specific therapy for late stage prostate cancer patients with skeletal metastases.

Although, as a bone-seeker, $^{223}$Ra shows significant clinical benefit for patients its activity is limited to the bone metastases and is not targeting soft tissue metastases.

Several carrier molecules for radioligand targeting of prostate specific membrane antigen (PSMA) exists. Lutetium-177 labeled PSMA-617 ($^{177}$Lu-PSMA-617) is the compound in most advanced clinical development stage for use in radionuclide therapy.

This molecule works in a suitable manner and give relevant tumor to normal tissue ratios for longer lived (i.e. a half-life of a few days) radionuclides, including $^{177}$Lu and $^{225}$Ac, but at early times points (typically a few hours after injection) shows high uptake in kidneys. With shorter lived radionuclides like $^{212}$Pb (half-life of 10.6 hours), the initial kidney uptake represents a potential toxicity problem.

It is therefore advantageous to use a PSMA-ligand with less kidney uptake, but this should not compromise the tumor uptake. The PSMA ligand molecules are made up of (1) a PSMA-binding region, (2) a linker region and (3) a chelator, whereby the linker region connects the (1) and (3). The linker region also is used to adjust molecular size and polarity etc to affect the in vivo distribution properties. The PSMA-binding region (motif) used in PSMA-617 is a structure that can be found in several molecules of this class, developed by several different inventors and researchers, including PSMA-11 and PSMA I&T as well as $^{131}$I and $^{211}$At labelled PSMA binding ligands.

New compounds that contain a PSMA region are warranted because at current all ligands in testing have challenges, including a relatively low radiobiological effectiveness (RBE) and suboptimal biodistribution.

There is also a need for an improved alpha emitter that can target both the bone metastases and the soft tissue metastases.

The present invention relates to compounds that addresses these challenges.

SUMMARY OF THE INVENTION

An aspect of the present invention relates to the complex of the present invention, wherein the compound X is linked to a radionuclide, such as $^{212}$Pb or $^{227}$Th, by a chelating moiety Z.

In one embodiment of the present invention is the radionuclide $^{212}$Pb.

In another embodiment of the present invention is the radionuclide $^{227}$Th.

The chelating moiety Z may be selected from the group consisting of acyclic chelators, cyclic chelators, cryptands, crown ethers, porphyrins or cyclic or noncyclic polyphosphonates, DOTMP, EDTMP, bisphosphonate, DOTA, a DOTA derivative, pamidronate conjugated to DOTA, TCMC, a TCMC derivative, pamidronate conjugated to TCMC, antibody-conjugated-DOTA, antibody-conjugated-TCMC, HBED-CC, NOTA, NODAGA, TRAP, NOPO, PCTA, DFO, DTPA, CHX-DTPA, AAZTA, DEDPA, and oxo-Do3A.

In one embodiment of the present invention is the linker DOTA or a DOTA derivative.

In another embodiment of the present invention is the linker TCMC or a TCMC derivative.

For $^{227}$Th are octadentate hydroxypyridinone-containing ligands, such as 3,2-HOPO, particularly suitable.

An aspect of the present invention relates to the radiopharmaceutical composition according to the present invention for use as a medicament.

An aspect of the present invention relates to the radiopharmaceutical composition according to the present invention for use in the treatment of soft tissue and or skeletal disease.

In one embodiment of the present invention is the skeletal disease selected from the group consisting of skeletal metastases from cancers to the breast, prostate, kidneys, lung, bone, or multiple myeloma, or non-cancerous diseases causing undesired calcification including ankylosing spondylitis.

FIGURES

Figure Text

DETAILED DESCRIPTION OF THE INVENTION

Some Abbreviations Used

Figure 1:
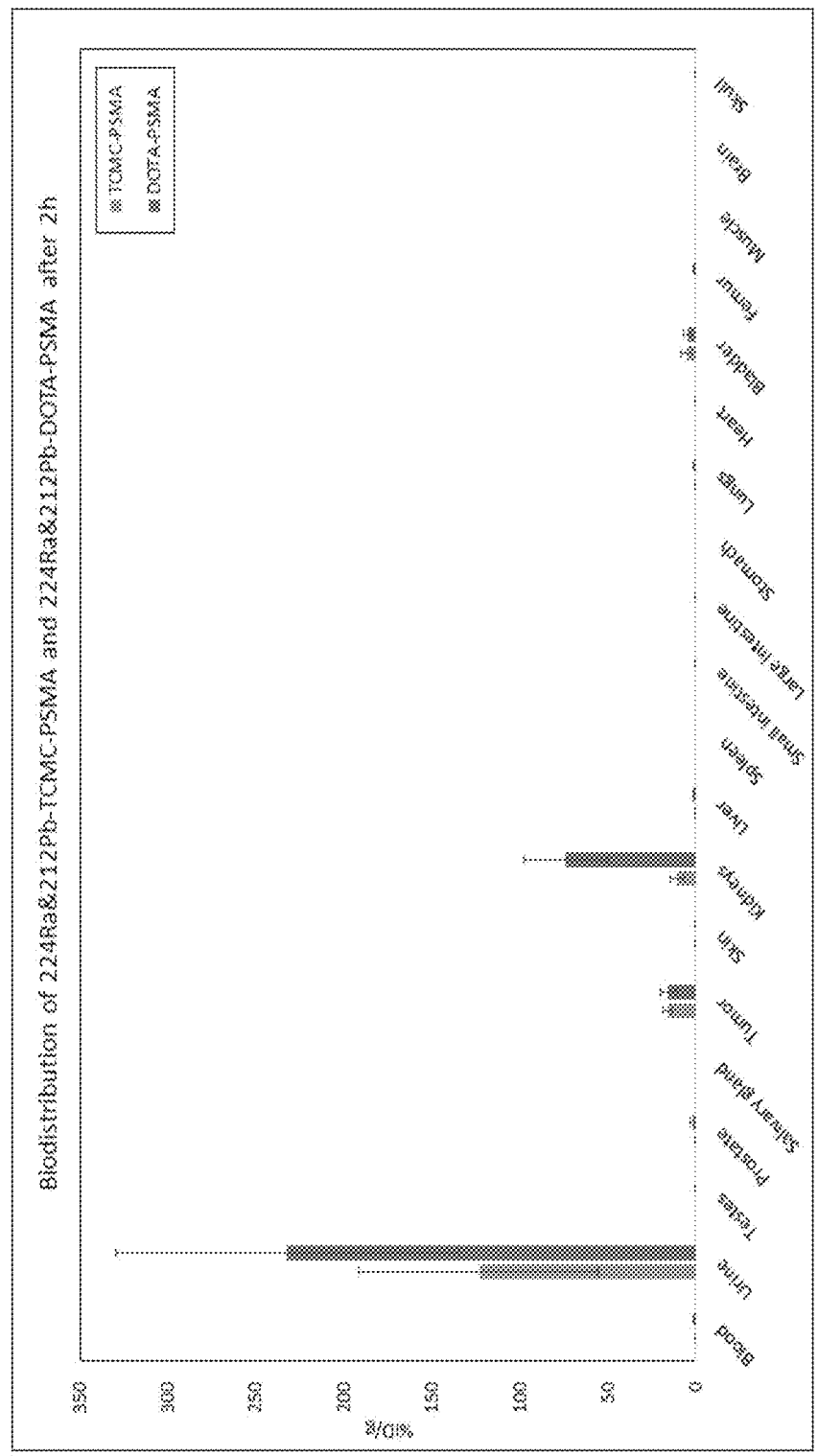
FIG. 1 shows biodistribution of $^{212}$Pb 2 hours after injecting $^{212}$Pb-labeled p-SCN-Bn-TCMC-PSMA ligand 1 and PSMA-617 respectively, in the presence of $^{224}$Ra.

Peptide mimetic—also termed peptidomimetic, is a small protein-like chain designed to mimic a peptide. They typically arise either from modification of an existing peptide, or by designing similar systems that mimic peptides, such as peptoids and β-peptides. Irrespective of the approach, the altered chemical structure is designed to advantageously adjust the molecular properties such as, stability or biological activity. This can have a role in the development of drug-like compounds from existing peptides. These modifications involve changes to the peptide that will not occur naturally (such as altered backbones and the incorporation of nonnatural amino acids). Based on their similarity with the precursor peptide, peptidomimetics can be grouped into four classes (A-D) where A features the most and D the least similarities. Classes A and B involve peptide-like scaffolds, while classes C and D include small molecules.

PSMA—Prostate-specific membrane antigen. Synonyms PSMA, Prostate Specific Cancer Antigen, PSM, FGCP, FOLH, GCP2, mGCP, GCPII, NAALAD1, NAALAdase, FOLH1, Glutamate carboxypeptidase 2, Glutamate carboxypeptidase II, Membrane glutamate carboxypeptidase, N-acetylated-alpha-linked acidic dipeptidase I, Pteroylpoly-gamma-glutamate carboxypeptidase, Folylpoly-gamma-glutamate carboxypeptidase, Folate hydrolase 1, Prostate-specific membrane antigen, Cell growth-inhibiting protein 27

DOTMP—1,4,7,10-tetraazacyclododecane-1,4,7,10-tetra (methylene phosphonic acid)

EDTMP—ethylenediamine tetra(methylene phosphonic acid)

EDTA—ethylenediaminetetraacetic acid p-SCN-Bn-DOTA—2-(4-isothiocyanatobenzyl)-1,4,7, 10-tetraazacyclododecane-1,4,7,10-tetraacetic acid DOTA—1,4,7,10-tetraazacyclododecane-1,4,7,10-tetraacetic acid and also used for benzyl-1,4,7,10-tetraazacyclododecane-1,4,7,10-tetraacetic acid (e.g. conjugated to monoclonal antibody)

p-SCN-Bn-TCMC—2-(4-isothiocyanotobenzyl)-1, 4, 7, 10-tetraaza-1, 4, 7, 10-tetra-(2-carbamonyl methyl)-cyclododecane TCMC—1, 4, 7, 10-tetraaza-1, 4, 7, 10-tetra-(2-carbamonyl methyl)-cyclododecane and also used for benzyl-1, 4, 7, 10-tetraaza-1, 4, 7, 10-tetra-(2-carbamonyl methyl)-cyclododecane (e.g. conjugated to monoclonal antibody)

mAb—monoclonal antibody.

HOPO—Me-3,2-HOPO, octadentate hydroxypyridinone for complexing 227Th, 4-((4-(3-(bis(2-(3-hydroxy-1-methyl-2-oxo-1,2-dihydropyridine-4-carboxamido)ethyl) amino)-2-((bis(2-(3-hydroxy-1-methyl-2-oxo-1,2-dihydropyridine-4-carboxamido)ethyl)amino)methyl)propyl) phenyl)amino)-4-oxobutanoic acid and derivatives.

Ligand 1—p-SCN-Bn-TCMC-PSMA ligand 1, p-SCN-Bn-TCMC-PSMA etc.

Ligand 2—p-SCN-Bn-DOTA-PSMA ligand 2, p-SCN-Bn-DOTA-PSMA etc

The same abbreviations are in the following used for acids, salts or partly or fully dissociated versions of the chelators.

The present invention relates to single and dual targeting property solutions based on a small molecular urea derivative as a prostate cancer cellular targeting agent for carrying $^{212}$Pb.

This may be used with purified $^{212}$Pb or in a dual targeting solution whereby $^{224}$Ra will act as a skeletal treatment and $^{212}$Pb-urea-derivative will act as a systemic therapy against cells expressing PSMA antigen which is associated mainly with advances metastatic prostate cancer, and to some extent also other types of cancer.

It is known in the field that urea based compounds conjugated to a chelator group can facilitate the targeting of radionuclides to PSMA expressing cells. Radionuclides that have been evaluated for radiotherapeutic purposes with PSMA targeting includes $^{177}$Lu, $^{211}$At, $^{213}$Bi, and $^{225}$Ac.

The invention is in the field of radiolabeled therapy agents. According to the invention, radiolabelled derivatives of urea based prostate-specific membrane antigen (PSMA) inhibitors are disclosed.

Thus, the present invention relates to a complex comprising a compound X linked to a radionuclide, such as $^{212}$Pb or $^{227}$Th, wherein the compound X is a peptide or peptidomimetic urea derivative suitable for targeting of PSMA expressing cells and tissues.

Linker

An aspect of the present invention relates to the complex of the present invention, wherein the compound X is linked to a radionuclide, such as $^{177}$Lu, $^{213}$Bi, $^{225}$Ac, $^{212}$Pb or $^{227}$Th, by a chelating moiety Z.

In one embodiment of the present invention is the radionuclide $^{212}$Pb.

In another embodiment of the present invention is the radionuclide $^{227}$Th.

In another embodiment of the present invention is the radionuclide $^{177}$Lu.

In a further embodiment of the present invention is the radionuclide $^{213}$Bi or $^{212}$Bi.

In yet another embodiment of the present invention is the radionuclide $^{225}$Ac.

It is to be understood that the complexing agent, or linker, or chelating moiety Z, according to the invention may also cover derivatives of the above-mentioned compounds (such as derivatives of EDTMP, DOTA, for example p-SCN-Bn-DOTA and TCMC, for example p-SCN-Bn-TCMC). It is of course to be understood that such derivatives must maintain the capability to complex $^{212}$Pb with a higher stability constant than to $^{224}$Ra.

The chelating moiety Z may be selected from the group consisting of acyclic chelators, cyclic chelators, cryptands, crown ethers, porphyrins or cyclic or noncyclic polyphosphonates, DOTMP, EDTMP and bisphosphonate derivatives, DOTA, a DOTA derivative such as p-SCN-Bn-DOTA, pamidronate conjugated to DOTA, TCMC, a TCMC derivative such as p-SCN-Bz-TCMC, pamidronate conjugated to TCMC, antibody-conjugated-DOTA, antibody-conjugated-TCMC, HBED-CC, NOTA, NODAGA, TRAP, NOPO, PCTA, DFO, DTPA, CHX-DTPA, AAZTA, DEDPA, and oxo-Do3A.

In one embodiment of the present invention is the linker DOTA or a DOTA derivative, such as p-SCN-Bn-DOTA.

In another embodiment of the present invention is the linker TCMC or a TCMC derivative, such as p-SCN-Bn-TCMC.

The complexing agent may be linked via the carbon backbone allowing all "binding arms" of the chelator molecule interact with the metal. Alternatively, one of the arms may be used as a linker.

Suitable chelators include DOTA derivatives such as p-isothiocyanatobenzyl-1,4,7,10-tetraazacyclododecane-1, 4,7,10-tetraacetic acid (p-SCN-Bz-DOTA) and DOTA-NHS-ester.

Thus, for p-SCN-Bn-DOTA or p-SCN-Bn-TCMC can the complexing agent be linked via the carbon backbone (C-backbone) to the rest of the compound.

In one embodiment is the linker an octadentate hydroxypyridinone-containing ligands, such as 3,2-HOPO. Such ligands will typically comprise at least one chelating group of the following substituted pyridine structure (I):

$$-17-R, \qquad I$$

Wherein R, is an optional N-substituent group and may thus be absent or may be selected from hydrocarbon, OH, 0-hydrocarbon, SH and S-hydrocarbon groups, where any or each hydrocarbon moiety is independently selected from short hydrocarbyl groups, such as C1 to C8 hydrocarbon, including C1 to C8 alkyl, alkenyl or alkynyl groups, or may be an OH or 0-hydrocarbon. R, may also comprise a linker moiety, as indicated below and/or may comprise a coupling moiety as also indicated below.

In Formula I, groups R2 to R6 may each independently be selected from H, OH, =0, short hydrocarbon (as described herein), a linker moiety (as described herein) and/or a coupling moiety (as described herein). Generally, at least one of groups R, to R6 will be OH. Generally, at least one of groups R2 to R6 will be =0.

Generally, at least one of groups R, to R6 will be a linker moiety. Preferably, exactly one of groups R2 to R6 will be =0. Preferably exactly one of groups R, to R6 will be OH. Preferably exactly one of groups R, to R6 will be a linker moiety (as described herein). The remaining groups R, to R6 may be any of those moieties indicated herein, but are preferably H. Where a linker moiety or any additional linker, template or chelating groups attached to a linker moiety do not comprise a coupling moiety then one of groups R, to R6 is preferably a coupling moiety (as described herein).

In a preferred embodiment, one of groups R, to R6 will be OH and one of R2 to will be =0 and the OH and =0 groups will be on neighbouring atoms of the ring.

Thus, in a preferred embodiment, OH and =0 may be on atoms 1,2; 2,3; 3,2; 3,4; or 4,3 respectively (numbering from the nitrogen as would be expected).

Octadentate ligands having at least one chelating moiety wherein OH and =0 groups are present at positions 3 and 2 respectively are highly preferred. The octadentate ligands may have 2, 3 or 4 such chelating groups, where 2 or 4 such groups are highly preferred.

In a special embodiment an urea derivative based PSMA targeting complex is labeled with $^{212}$Pb or $^{227}$Th in a mixture of bone-seeking $^{224}$Ra or $^{223}$Ra, respectively, for dual targeting by (1) PSMA cellular targeting and (2) targeting of skeletal metastases related bone synthesis by radium cations.

Complexing agents for $^{227}$Th including those described in WO2011098611, US20170319721, Ramdahl et al. (Bioorganic & Medicinal Chemistry Letters Volume 26, Issue 17, 1 Sep. 2016, Pages 4318-4321), and Hagemann et al. (Mol Cancer Ther. 2016 October; 15(10):2422-2431. Epub 2016 Aug. 17) conjugated to an urea derivative for PSMA targeting. The complexing agents mentioned herein are hereby incorporated by reference.

Thus, one embodiment of the present invention relates to a PSMA targeting urea derivative comprising a TCMC group, such as p-SCN-Bn-TCMC, for chelating $^{212}$Pb.

Another embodiment of the present invention relates to a PSMA targeting urea derivative comprising HOPO for chelating $^{227}$Th.

A further embodiment of the present invention relates to a PSMA targeting urea derivative comprising DOTA, such as p-SCN-Bn-TCMC, labeled with either $^{212}$Pb or $^{227}$Th.

In yet an embodiment, the complexing agent does not complex $^{224}$Ra or substantially complex $^{224}$Ra in the pharmaceutical composition.

In yet a further embodiment, the complexing agent complexes with a higher stability constant to $^{212}$Pb than to $^{224}$Ra.

In an embodiment, the stability constant for $^{212}$Pb is at least twice the affinity for $^{224}$Ra, such as at least four times higher, such as at least 8 times higher or such as at least 10 times higher.

In an embodiment said complexing agent is selected from the group consisting of, ligand-conjugated-DOTA, such as ligand-conjugated-p-SCN-Bn-DOTA, or ligand-conjugated-TCMC, such as ligand-conjugated-p-SCN-Bn-TCMC.

The ligand may be an antibody or polypeptide.

In a further embodiment, the amount of $^{224}$Ra and $^{212}$Pb is in radioactive equilibrium.

In yet a further embodiment, the activity ratio (in MBq) between $^{212}$Pb to $^{224}$Ra is between 0.5 and 2, such as 0.8-1.5, or such as 0.8-1.3, or preferably such as 0.9-1.15.

In the present context, the term "radioactive equilibrium" relates to the ratio in MBq between two radionuclides being the same or substantially the same over time. The term "activity ratio" e.g. between $^{212}$Pb and $^{224}$Ra relates to the ratio of MBq of $^{212}$Pb to $^{224}$Ra. In FIG. 5 is a table (table 2) showing the development of this activity ratio over time. It can be seen that after two days a radioactive equilibrium of 1.1 has been established for the activity ratio between $^{212}$Pb to $^{224}$Ra (7.3 divided by 6.8). Thus, in FIG. 5, it can also be seen that the radioactive equilibrium between $^{212}$Pb and $^{224}$Ra is reached after about 2 days.

In the present context, the terms "complexing agent", "scavenger", "linker", "chelating moiety Z", and "chelating agent" are used interchangeably. The terms relate to agents capable of forming complexes with $^{212}$Pb, preferably by chelation and with a significant strength as measured in test systems while radium is not significantly affected by the presence of the complex as measured in the test systems.

Test systems include in vivo biodistribution and in vitro cation exchanger or size retention and centrifuge concentration cartridge for chelate-antibody binding of radionuclide. Alternatively, thin layer chromatograpy may be used as a test system.

In the present context "scavenging" (or complexing) is defined as at least 50% bound according to thin layer chromatography (TLC), centrifuge concentration separation or bio-distribution profiles.

This means, as an example, at least 50% less blood uptake of $^{212}$Pb with a small molecular chelator. With an antibody-conjugated chelator, where blood uptake is not a reliable indicator, at least 50% bound according to TLC analyses.

In one embodiment of the present invention is at least 60% bound.

In another embodiment of the present invention is at least 70% bound.

In another embodiment of the present invention is at least 80% bound.

In another embodiment of the present invention is at least 85% bound.

In another embodiment of the present invention is at least 90% bound.

The compound or compounds may also be capable of complexing more radionuclides than $^{212}$Pb.

In one embodiment of the present invention, the compound and/or complex is at a concentration of 1 ng/mL to 1 g/mL.

In another embodiment of the present invention, the compound and/or complex is at a concentration of 100 ng to 10 mg/mL The complex can comprise one, two, three, four, five or more compounds.

In one embodiment is the solution in a volume of 100 μL to 1000 mL, such as 500 μL to 100 mL, 1 mL to 10 mL.

In one embodiment of the present invention is the radioactivity of the solution 1 kBq to 1 GBq, such as 10 kBq to 100 MBq, such as 100 kBq to 10 MBq.

In another embodiment of the present invention is the radioactivity of the solution 100 kBq to 100 MBq.

In another embodiment of the present invention, the complexing agent is conjugated to a compound selected from the group consisting of peptides and peptide mimetic urea derivatives with affinity for PSMA.

In another embodiment of the present invention, the complexing agent is the chelator TCMC, such as p-SCN-Bn-TCMC, or DOTA, such as p-SCN-Bn-DOTA, conjugated to a compound selected from the group consisting of a monoclonal antibody, a polyclonal antibody, an antibody fragment, a synthetic protein, a peptide, a hormone or hormone derivative or a vitamin or a vitamin derivative.

For dosing purposes, a pure $^{212}$Pb solution may be used. Alternatively, $^{224}$Ra in mixture with $^{212}$Pb may be used, the latter for dual targeting purposes, i.e., $^{224}$Ra targets bone metastases and $^{212}$Pb targets systemic cancer by its urea derivative carrier. If $^{224}$Ra comprising solutions are administered they may have been stored for some time, e.g., 1 day or more preferably at least two days, such as 1-2 days or 1-3 days, to reach equilibrium between $^{224}$Ra and $^{212}$Pb/$^{212}$Bi. This will ensure $^{212}$Pb to $^{224}$Ra activity ratios between 0.83 and 1.14. This can, e.g., be accomplished by the manufacturer by simply retaining the product for a day or so before shipment.

Alternatively, $^{212}$Pb may be added to $^{224}$Ra solutions to obtain a specific radionuclide ratio. E.g. if the soft tissue tumor burden is much higher than the skeletal tumor burden, a pure $^{212}$Pb preparation or a solution with a high $^{212}$Pb to $^{224}$Ra ratio may be used.

The non-overlapping side effect profile of cationic radium and alpha emitters conjugated to PSMA binding urea-derivatives makes a mixture of $^{224}$Ra cation and $^{212}$Pb-PSMA targeting agent for dual targeting particularly attractive. This is because more modest dosing of each compound can be used to produce antitumor activity, since, at least for the skeletal component, the two different compounds will target the lesions independently.

It is important to keep radium as mainly un-complexed, or weakly complexed cation as this ensures a maximum uptake in bone and bone metastases and also ensures favourable excretion of eliminated product mainly through the intestines.

By adding complexing agent to a solution of radium the radioactive daughter can be made bone- or tumor-seeking and increase the therapeutic potential of the radium solution instead of being a health hazard. It should be a complexing agent that does not negatively affect the bone-seeking properties of radium, though. For example, can a TCMC-labeled urea derivative scavenge $^{212}$Pb produced in the radium solution during transport and storage between the production site and the hospitals whereby the product is going to be administered.

Although it is possible to reduce the susceptibility by adding radiolytic inhibitors, tumor targeting peptides and peptide mimetics are often more susceptible to radiolysis and should probably be supplied in a kit format whereby they are added a few hours to a few minutes before administration of $^{224}$Ra solutions with relatively long shelf-lives.

It is known in the field that calixarenes and EDTA to some extent can complex radium and also complex lead and bismuth. However, in the current work we found chelators that would leave radium mainly uncomplexed or weakly complexed, as determined by in vivo biodistribution measurements, while being able to rapidly and with relevant stability, complex the longest living daughter $^{212}$Pb. The selective complexation can be used to make at least lead bone- or tumor-seeking while maintaining the favourable properties of radium in terms of treating sclerotic diseases, like skeletal metastases. The $^{212}$Pb complex that targets bone or tumor cells generates the alpha emitter $^{212}$Bi from the decay of $^{212}$Pb. Thus, the beta emitter $^{212}$Pb is used as an indirect alpha source for irradiating the targeted cells or tissue. Other potential chelates which could be suitable for $^{224}$Ra daughter nuclide scavenging besides TCMC and DOTA includes but are not limited to phorphyrins, DTPA and DTPA derivatives and also carboxyl linked DOTA.

Lead-212 is by far the longest living of the progenies from $^{224}$Ra and this is the most important to complex, as it is an in vivo generator for the short-lived alpha-emitter $^{212}$Bi. If a $^{212}$Pb-chelate is taken up in bone or in tumor cells $^{212}$Bi will also likely be retained in the target. In a $^{224}$Ra solution in equilibrium with progenies there will be more than 10 times of $^{212}$Pb vs. $^{212}$Bi atoms. Thus, the amount of radiation generated from the $^{212}$Bi atoms in these solutions are modest and probably not of a toxicologically importance compared with $^{224}$Ra and $^{212}$Bi decay series. The amount of $^{212}$Bi is comparable to that of the $^{211}$Pb which indirectly produces an alpha particle in the $^{223}$Ra series and this has not been of a significant problem for the registration and clinical use of $^{223}$Ra in equilibrium with progenies.

If, however, a high degree of chelation also of $^{212}$Bi in an injectate should be needed, it may at least in some instances be necessary to add a stabilizing agent like NaI or HI since bismuth in aqueous solutions tends to exist in a state less suitable for chelation.

When comparing with current approved alpha-pharmaceutical for treatment of skeletal metastases, i.e., $^{223}$Ra, the novel solutions described herein could give, in one of the embodiment, a product with improved properties for treatment of skeletal metastases since the daughter nuclide can be made targetable to circulating cancer cells and, to some extent, also soft tissue metastases. This may prevent recurrence from cancer recolonization of the skeleton due to CTC's.

Another aspect is that the shorter half-life of $^{224}$Ra vs. $^{223}$Ra may actually be of some benefit as the radium is embedded in the bone matrix. Because of the high density of the bone mineral the range of alpha-particles is strongly reduced in bone vs. soft tissues. Especially in rapid mineralizing areas like osseous cancer metastases, the embedment process may be of significance when using a volume-seeking alpha-pharmaceutical.

Therefore, $^{224}$Ra could improve the tumor dose since, on average, it will be less embedded at the time of decay.

Diseases by which the novel $^{212}$Pb solutions with or without $^{224}$Ra may be used include but are not limited to primary and metastatic cancers, autoimmune diseases and artherioschlerosis. The product may be administered intravenously or locally, including intraperitoneally, or in limb perfusion settings.

The chelators used in the novel solutions may be acyclic as well as cyclic chelators and cryptands, crown ethers, porphyrins or cyclic- or noncyclic polyphosphonates including DOTMP and EDTMP. Also a bisphosphonate, e.g., pamidronate, conjugated to DOTA, TCMC or similar may be used as scavenger in the $^{224}$Ra solution.

One may argue that the amount of $^{212}$Pb in therapeutic $^{224}$Ra solution may be moderate to modest (i.e., at equilibrium about 1.1 times that of $^{224}$Ra). If one assumes similar dosing of $^{224}$Ra as is done with $^{223}$Ra in patients but correct for the half-life difference, roughly 150 kBq per kg of bodyweight would be the administered dose.

At equilibrium this would translate into a $^{212}$Pb-antibody conjugate dosage of 11.5 MBq in 5 liters of blood in a 70-kg patient (if $^{212}$Pb is quantitatively chelated). The number of circulating tumor cells is typically less than 10 cells per ml, thus in 5 l blood there are less than 50 000 tumor cell in total. If only 1 in 100 000 of the injected $^{212}$Pb-antibody conjugate molecules binds to the tumor cells this would mean at least 0.0023 Bq per cell, equivalent to approximately 127 $^{212}$Pb atoms bound per cell, which would be highly destructive as it has been reported that a mean of 25 cell bound $^{212}$Pb per cell would kill 90% of a cell population.

Compounds

An aspect of the present invention relates to a compound X linked to a chelating moiety Z is defined by the formula I:

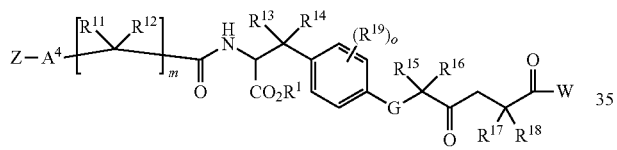

Formula I or a pharmaceutically acceptable salt thereof, wherein

W is a PSMA-targeting ligand;

$A^4$ is a bond or a divalent linking moiety comprising 1 to 10 carbon atoms in a chain, a ring, or a combination thereof, wherein at least one carbon atom is optionally replaced with O, —$NR^3$—, or —C(O)—;

G is C=O, C=S, C—$NH_2$, or C—$NR^3$;

$R^1$ is hydrogen or a carboxylic acid protecting group;

$R^3$ is selected from the group consisting of hydrogen, alkyl, cycloalkyl, heterocycloalkyl, aryl, alkylaryl, and heteroaryl.

$R^{11}$, $R^{12}$, $R^{13}$, $R^{14}$, $R^{15}$, and $R^{16}$ are each independently hydrogen, alkyl, alkoxyl, or $R^{17}$ and $R^{18}$ are each independently hydrogen, alkyl, aryl, or alkylaryl;

$R^{19}$ is selected from the group consisting of alkyl, alkoxyl, halide, haloalkyl, and CN;

m is an integer from 1 to 6; and o is an integer from 0 to 4, wherein when o is greater than 1, each $R^{19}$ is the same or different.

An aspect of the present invention relates to a complex according to the present invention, or a pharmaceutically acceptable salt thereof, wherein $A^4$ is a bond, $(CH_2)_n$, —HC(O)—, —$(OCH_2CH_2)_n$—, —$(HCH_2CH_2)_n$—, —H(CO)$CH_2$—, —HC(O)$CH_2$ $(OCH_2CH_2)_n$—, or —HC(O)$CH_2(HCH_2CH_2)_n$—; and L is a bond, $(CH_2)_n$, —$(OCH_2CH_2)_n$—, —$(HCH_2CH_2)_n$—, or —C(O)$(CH_2)_n$—;

wherein n is independently 1, 2, or 3.

An aspect of the present invention relates to a complex according to the present invention, or a pharmaceutically acceptable salt thereof, wherein $A^4$ is a bond, —(OCH$_2$ CH$_2$)$_n$—, or —HC(O)CH$_2$(OCH$_2$CH$_2$)$_n$—; and L is a bond, or —(OCH$_2$CH$_2$)$_n$—;

wherein n is independently 1 or 2.

An aspect of the present invention relates to a complex according to the present invention, or a pharmaceutically acceptable salt thereof, wherein W has the structure:

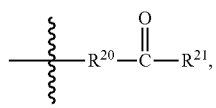

wherein $R^{20}$ and $R^{21}$ are each independently an amino acid residue linked via an amino group thereof to the adjacent —C(O)— group.

An aspect of the present invention relates to a complex according to the present invention, or a pharmaceutically acceptable salt thereof, wherein W has the structure:

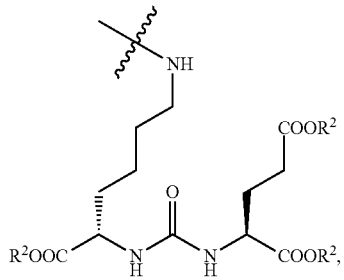

wherein R is hydrogen or a carboxylic acid protecting group.

An aspect of the present invention relates to a complex according to the present invention, or a pharmaceutically acceptable salt thereof, having the structure:

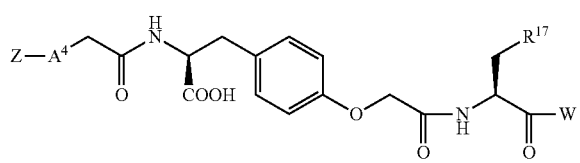

or a pharmaceutically acceptable salt thereof, wherein $R^{17}$ is aryl.

An aspect of the present invention relates to a complex according to the present invention, or a pharmaceutically acceptable salt thereof, wherein the complex is PSMA-617:

11

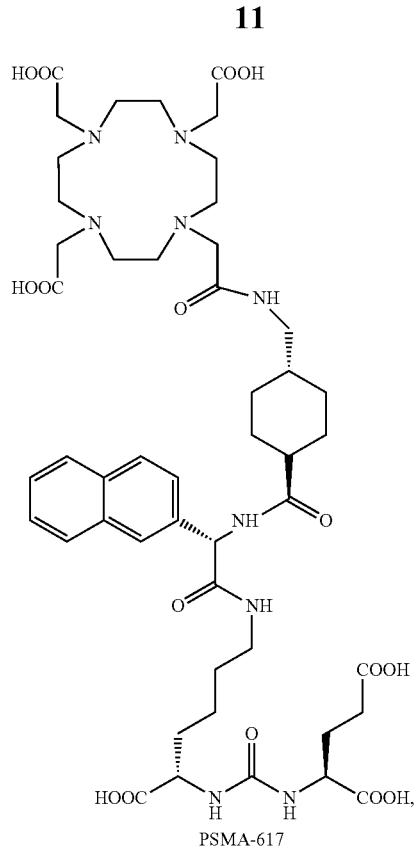

PSMA-617

With a radionuclide such as $^{212}$Pb linked/chelated to four N.

An aspect of the present invention relates to a complex according to the present invention, wherein the DOTA unit, such as p-SCN-Bz-DOTA, is substituted with a TCMC unit, such as p-SCN-Bz-TCMC.

The linker in PSMA-617 may also be covalently linked to from a C-atom in the backbone instead of link to N as can be seen in the above figure.

Thus, the urea derivative may have backbone C-linked or N-linked DOTA or TCMC conjugation.

For a backbone-C linked p-SCN-Bn-DOTA or p-SCN-Bn-TCMC conjugation is the compound:

12

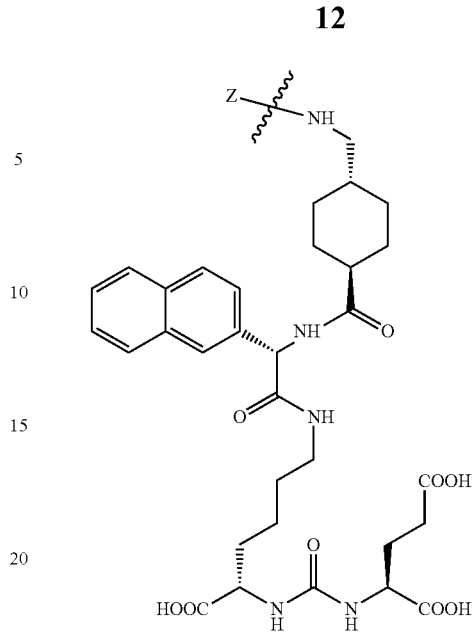

Wherein Z is:

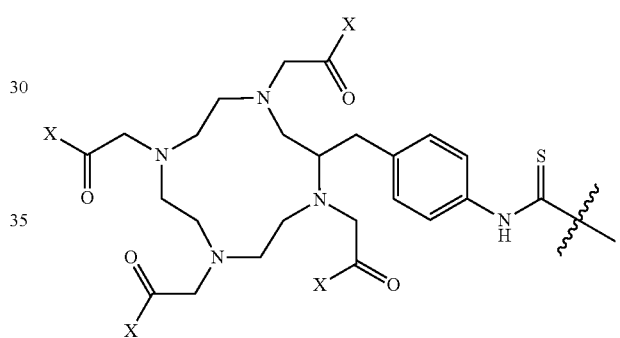

And wherein X is: —OH or NH$_2$.

X is —OH for p-SCN-Bn-DOTA and X is NH$_2$ for p-SCN-Bn-TCMC.

This means that the formula for backbone-C linked p-SCN-Bn-DOTA or p-SCN-Bn-TCMC will be:

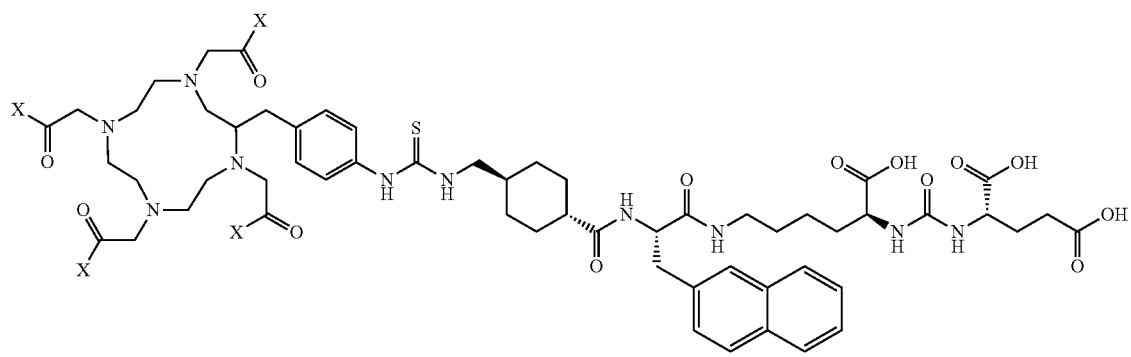

wherein X is: —OH or NH$_2$.

Backbone-C linked p-SCN-Bn-DOTA is:

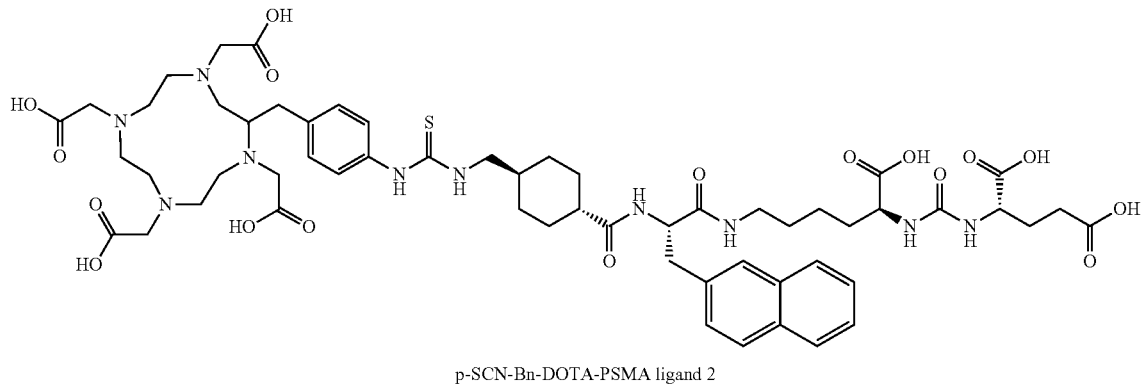 [SMILES: O=C(O)CC[C@H](NC(=O)N[C@@H](CCCCNC(=O)[C@H](Cc1ccc2ccccc2c1)NC(=O)[C@H]1CC[C@H](CNC(=S)Nc2ccc(CC3CN(CC(=O)O)CCN(CC(=O)O)CCN(CC(=O)O)CCN3CC(=O)O)cc2)CC1)C(=O)O)C(=O)O]

p-SCN-Bn-DOTA-PSMA ligand 2

Thus, an aspect of the present invention related to a compound which is p-SCN-Bn-DOTA-PSMA ligand 2.
Backbone-C linked p-SCN-Bn-TCMC is:

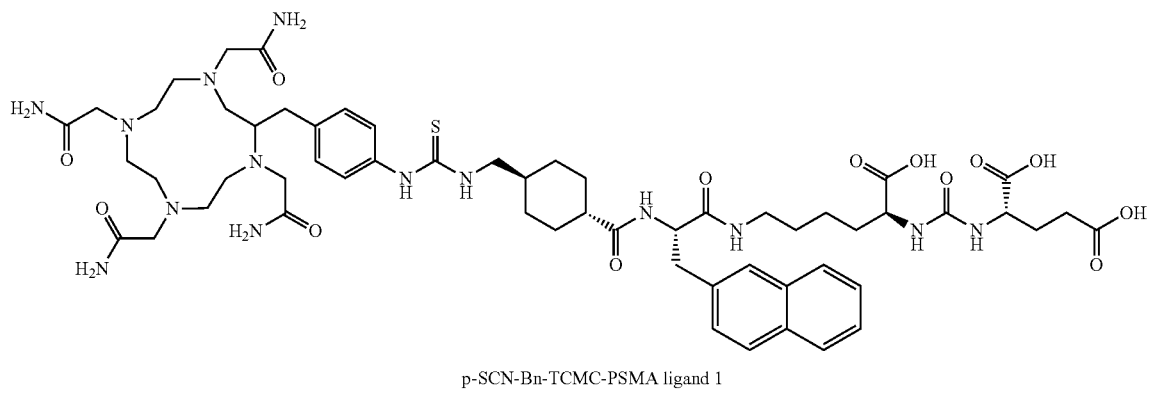 [SMILES: NC(=O)CN1CCN(CC(N)=O)CCN(CC(N)=O)C(Cc2ccc(NC(=S)NC[C@H]3CC[C@H](C(=O)N[C@@H](Cc4ccc5ccccc5c4)C(=O)NCCCC[C@H](NC(=O)N[C@@H](CCC(=O)O)C(=O)O)C(=O)O)CC3)cc2)CN(CC(N)=O)CC1]

p-SCN-Bn-TCMC-PSMA ligand 1

Thus, an aspect of the present invention related to a compound which is p-SCN-Bn-TCMA-PSMA ligand 1 or p-SCN-Bn-DOTA-PSMA ligand 2 as disclosed above, and the examples.

The p-SCN-Bn-TCMC-PSMA ligand (ligand 1) and p-SCN-Bn-DOTA-PSMA ligand (ligand 2) (as shown in the examples) is linked via the carbon backbone (C-backbone) to the rest of the compound and has an extended linker region including a isothiocyanato-benzyl linker and also uses a carbon substituted chelator with all 4 chelator arms free as opposed to PSMA-617 which has a shorter linker region and uses one of the chelator arms as linker attachment. It is shown in the later examples herein that these differences cause a significant different biodistribution of the radiolabelled product, making it more suitable for targeting of $^{212}$Pb to PSMA-expressing tumors, as it reduces kidney exposure compared to PSMA-617.

In one embodiment of the present invention can the compounds of the present invention, such as p-SCN-Bn-TCMC-PSMA ligand 1 and p-SCN-Bn-DOTA-PSMA ligand 2, be in the form of a trifluoroacetic acid salt.

CTT1401 and CTT1403 and derivatives (Choy et al, 2017) with TCMC or DOTA variants may also be used with $^{212}$Pb in the complexes of the present invention.

By preparing a PSMA binding Urea derivative according to the present invention with a readily accessible amino group or another group suitable for conjugation, p-SCN-Bn-TCMC can be conjugated to the PSMA binding compound. Subsequent purification may be needed before radiolabelling with $^{212}$Pb with or without $^{224}$Ra in solution.

Thus, in one embodiment of the present invention is the linker p-SCN-Bn-TCMC. One embodiment of the present invention relates to a complex according to the present invention, wherein the linker-chelator is p-SCN-Bn-TCMC. One embodiment of the present invention relates to a complex according to the present invention, wherein the linker is p-SCN-Bn-DOTA. In other words -p-SCN-Bn- is the end part of the linker region which is attached to the TCMC or DOTA chelator group via the carbon backbone.

Human serum albumin can be used to prolong the half-life of drugs. Thus, in an embodiment the $^{212}$Pb-labeled PSMA binding urea derivative according to the present invention further comprises a group that can associate with albumin to increase the circulation half-life of the radiolabeled product.

A further embodiment of the present invention relates to a complex according to the present invention, wherein $^{212}$Pb-labeled PSMA binding urea derivative according to the present invention further comprises human serum albumin that has been directly conjugated to the complex, or is associated to the complex, for example through liposomes.

Pharmaceutical Compositions

An embodiment of the present invention relates to a solution comprising the compound and/or the complex of the invention. The solution can also be a pharmaceutical composition.

Usually is an important element of a pharmaceutical composition a buffer solution, which to a substantial degree maintain the chemical integrity of the radioligand and is being physiologically acceptable for infusion into patients.

In one embodiment of the present invention, the pharmaceutical composition comprises one or more pharmaceutically acceptable carriers and/or adjuvants.

Acceptable pharmaceutical carriers include but are not limited to non-toxic buffers, fillers, isotonic solutions, etc. More specifically, the pharmaceutical carrier can be but are not limited to normal saline (0.9%), half-normal saline, Ringer's lactate, 5% Dextrose, 3.3% Dextrose/0.3% Saline. The physiologically acceptable carrier can contain an antiradiolytic stabilizer, e.g., ascorbic acid, which protect the integrity of the radiopharmaceutical during storage and shipment.

An aspect of the present invention relates to a pharmaceutical composition comprising the complex according to the present invention, and a diluent, carrier, surfactant, and/or excipient.

An aspect of the present invention relates to single agent $^{212}$Pb-labeled ligand. This would be the compound of the present invention complexed with $^{212}$Pb and without any further radionuclides, such as $^{224}$Ra.

An aspect of the present invention relates to a dual targeting solution containing $^{212}$Pb-labeled ligand and cationic or weakly complexed $^{224}$Ra. This would be the compound of the present invention complexed with $^{212}$Pb with $^{224}$Ra present as cationic or weakly complexed $^{224}$Ra.

An aspect of the present invention relates to a pharmaceutical composition comprising the compound and/or the complex according to the present invention, further comprising $^{224}$Ra. $^{224}$Ra can be cationic. The addition of $^{224}$Ra allows for dual targeting for example when present together with $^{212}$Pb.

An aspect of the present invention relates to a pharmaceutical composition comprising the complex according to the present invention, wherein the radioactivity is 100 kBq to 100 MBq per dose.

An aspect of the present invention relates to a pharmaceutical composition comprising the complex according to the present invention, wherein the amount of $^{224}$Ra and $^{212}$Pb is in radioactive equilibrium.

An aspect of the present invention relates to a pharmaceutical composition comprising the complex according to the present invention, wherein the activity ratio (MBq) between $^{212}$Pb to $^{224}$Ra is between 0.5 and 2, such as 0.8-1.5, or such as 0.8-1.3, or preferably such as 0.9-1.15.

Kits

The solution should be made physiologically suitable for injections either at a centralized production site or be made up by a kit system of typically 2-4 vials whereby being physiologically suitable for injection after combination of the kit vials.

An aspect of the present invention relates to a kit comprising a first vial comprising a radiopharmaceutical composition according to the present invention, and a second vial comprising a neutralizing solution to adjust pH and/or isotonicity of the radiopharmaceutical composition prior to administration to a patient.

For, e.g., a monoclonal antibody, it is usually advisable be keep the self-dose of the alpha particle producing radiopharmaceutical solution below 0.5 kGy to avoid reduced binding properties due to radiolysis. Thus, a kit system whereby chelator conjugated ligand is added to the $^{224}$Ra (including daughters) solution a few hours to 10 minutes before injection is advised for concentrated solutions intended for remote shipping, depending of the radiolytic resistance of the radioligand that is generated.

An aspect of the present invention relates to a kit comprising a first vial comprising a $^{224}$Ra solution; a second vial comprising a complexing agent selected from the group consisting of p-SCN-Bn-DOTA-PSMA ligand, p-SCN-Bn-TCMC-PSMA ligand, acyclic chelators, cyclic chelators, cryptands, crown ethers, porphyrins or cyclic or noncyclic polyphosphonates, DOTMP, EDTMP, bisphosphonate derivatives, DOTA, a DOTA derivative, pamidronate conjugated to DOTA, TCMC, a TCMC derivative, pamidronate conjugated to TCMC, antibody-conjugated-DOTA, antibody-conjugated-TCMC, HBED-CC, NOTA, NODAGA, TRAP, NOPO, PCTA, DFO, DTPA, CHX-DTPA, AAZTA, DEDPA, and oxo-Do3A, wherein the complexing agent is capable of complexing a daughter nuclide of $^{224}$Ra, such as $^{212}$Pb, and wherein the complexing agent does not complex $^{224}$Ra in the pharmaceutical solution; and optionally, instructions for mixing the first vial and the second vial, thereby forming a pharmaceutical composition ready to be administered to a patient 1 minute to 12 hours after mixing.

In one embodiment of the present invention is the kit for use as a medicament.

In a specific embodiment, the term "$^{224}$Ra solution" is to be understood as $^{224}$Ra is free in the solution and not coupled to e.g. a surface such as a resin.

In an embodiment, the kit comprises a third vial comprising a neutralizing solution to adjust pH and/or isotonicity of the radiopharmaceutical solution prior to administration to a patient.

In yet a preferred embodiment, the amount of $^{224}$Ra and $^{212}$Pb is in radioactive equilibrium in the first vial.

In yet another preferred embodiment the activity ratio (MBq) between $^{212}$Pb to $^{224}$Ra in the first vial is between 0.5 and 2, such as 0.8-1.5, or such as 0.8-1.3, or such as 0.9-1.15.

In yet another embodiment the first vial has a radioactivity in the range 100 kBq to 100 MBq.

In one embodiment of the present invention, the chelator conjugated ligand is added to the $^{224}$Ra (including daughters) solution 30 min to 5 hour before injection, such as 1-3 hours before injection.

In one embodiment of the present invention, the chelator conjugated ligand is added to the $^{224}$Ra (including daughters) solution 1 min to 20 min before injection.

In one embodiment of the present invention, the chelator conjugated ligand is added to the $^{224}$Ra (including daughters) solution 1 min to 10 min before injection.

A kit with a chelate labelled protein or peptide in one vial and a $^{224}$Ra solution in another vial whereby the content of the two are mixed 12 hours to 1 minute before administration also forms part of the invention. In an embodiment, the mixing takes place a few hours (such as 5) to 30 minutes before administration to a patient as to bind $^{212}$Pb and or $^{212}$Bi to the chelate.

In one embodiment of the present invention, the content of the two are mixed 30 min to 1 hour before injection.

In one embodiment of the present invention, the content of the two are mixed 1 min to 20 min before injection.

In embodiment of the present invention, the content of the two are mixed 1 min to 10 min before injection.

Optionally, a third vial containing a liquid used for dilution and isotonicity adjustment before administration of the radiopharmaceutical solution could be used. This third vial may contain EDTMP, which could chelate $^{212}$Bi, if needed.

Medical Applications

An aspect of the present invention relates to the radiopharmaceutical composition according to the present invention for use as a medicament.

In one embodiment of the present invention is the disease cancer.

An aspect of the present invention relates to the radiopharmaceutical composition according to the present invention for use in the treatment of soft tissue and/or skeletal disease. The treatment is focused on PSMA-expressing disease including soft tissue- and skeletal disease.

In one embodiment of the present invention is the skeletal disease selected from the group consisting of soft tissue and or skeletal metastases from cancers to the breast, prostate, kidneys, lung, bone, or multiple myeloma.

In one embodiment of the present invention is the cancer prostate cancer. The cancer can also be breast cancer. The cancer can be kidney cancer. The cancer can also be lung cancer. The cancer can also be bone cancer. The cancer can also be multiple myeloma. The cancer can be metastases from these types of cancer.

In one embodiment of the present invention is the solution administered at a dose in the range 50-150 kBq per kg of bodyweight, such as 50-100 kBq per kg of bodyweight.

An aspect of the present invention relates to a method of treatment of malignant or non-malignant disease by administration of a radiopharmaceutical composition according to the present invention to an individual in need thereof.

This may be used with purified $^{212}$Pb-labeled ligand or in a dual targeting solution whereby $^{224}$Ra will act as a skeletal treatment, and $^{212}$Pb-urea-derivative will act as a systemic therapy against cells the expressing PSMA antigen which is associated with advances metastatic prostate cancer.

Thus, the complexes and the solutions of the present invention can be used in the treatment of metastatic prostate cancer.

Another embodiment of the present invention relates to a pharmaceutical solution with dual targeting properties whereby $^{212}$Pb is complexed by a urea based PSMA targeting agent as disclosed herein, and cationic $^{224}$Ra is targeting bone metastases though calcium mimetic bone incorporation.

Methods for Preparation

An aspect of the present invention relates to a method for providing a radiopharmaceutical composition according to the present invention, the method comprising providing a first solution wherein the amount of $^{224}$Ra and $^{212}$Pb is in radioactive equilibrium; providing a second solution comprising a complexing agent that is selected from the group consisting of p-SCN-Bn-DOTA-PSMA ligand, p-SCN-Bn-TCMC-PSMA ligand, acyclic chelators, cyclic chelators, cryptands, crown ethers, porphyrins or cyclic or noncyclic polyphosphonates, DOTMP, EDTMP, bisphosphonate, DOTA, a DOTA derivative, pamidronate conjugated to DOTA, TCMC, a TCMC derivative, pamidronate conjugated to TCMC, antibody-conjugated-DOTA, antibody-conjugated-TCMC, HBED-CC, NOTA, NODAGA, TRAP, NOPO, PCTA, DFO, DTPA, CHX-DTPA, AAZTA, DEDPA, and oxo-Do3A, wherein the complexing agent is capable of complexing a daughter nuclide of $^{224}$Ra, such as $^{212}$Pb, and wherein the complexing agent does not complex $^{224}$Ra; and mixing the first composition and the second composition, thereby providing a pharmaceutical composition according to the present invention.

PSMA Derivatives

PSMA (also named Prostate Specific Cancer Antigen, PSM, FGCP, FOLH, GCP2, mGCP, GCPII, NAALAD1, NAALAdase, FOLH1, Glutamate carboxypeptidase 2, Glutamate carboxypeptidase II, Membrane glutamate carboxypeptidase, N-acetylated-alpha-linked acidic dipeptidase I, Pteroylpoly-gamma-glutamate carboxypeptidase, Folylpoly-gamma-glutamate carboxypeptidase, Folate hydrolase 1, Prostate-specific membrane antigen, Cell growth-inhibiting protein 27) is a prostate epithelial cell membrane antigen of type II transmembrane protein and consist of a short NH2-terminal cytoplasmic domain, hydrophobic transmembrane region, and a large extracellular domain. PSMA is an enzyme that in humans is encoded by the FOLH1 (folate hydrolase 1) gene. Human GCPII contains 750 amino acids and weighs approximately 84 kDa.

Expression of PSMA is restricted to a few healthy tissues such as lacrimal and salivary glands, proximal renal tubules, epididymis, ovary, the luminal side of the ileum-jejunum and astrocytes within the central nervous system (CNS); healthy prostate gland expresses comparatively little PSMA, which is confined within the apical epithelium of secretory ducts. In these non-malignant tissues, uptake of PSMA-targeted probes may be limited by an intact blood-brain barrier, a healthy proximal small bowel lumen, and truncated cytoplasmic expression of PSMA within normal prostate. PSMA is most associated with high grade androgen independent, metastatic disease, although PSMA is expressed in most primary prostate tumors regardless of androgen status.

Small molecular PSMA inhibitors are zinc binding compounds and can be classified into three types 1) phosphonate-, phosphate-, and phosphoramidate compounds; 2) thiols; and 3) ureas. The urea derivatives seem to have particularly interesting properties as carrier for radionuclides for diagnosis and therapy.

The current invention relates to use of $^{212}$Pb-urea derivatives. It may be combined with androgen deprivation therapy to enhance PSMA expression for better uptake of radioligand (Bakht et al, 2017).

Activity Level

If a $^{212}$Pb-labeled urea derivative is used alone, the activity level would typically be between 1 MBq and 500 MBq per patient, more typically 10-100 MBq per patient.

If $^{224}$Ra in equilibrium with $^{212}$Pb complexed with a PSMA binding urea derivative the dosing would typically be between 0.1 MBq and 100 MBq per patient, more typically between 1 and 20 MBq per patient.

In a special embodiment an urea derivative based PSMA targeting complex according to the present invention, labeled with $^{227}$Th, which produces bone-seeking $^{223}$Ra for dual targeting.

The $^{227}$Th may be pure or containing various amounts of $^{223}$Ra eg. 10%, 50%, 100% or 250% of $^{223}$Ra compared to $^{227}$Th.

General

It should be understood that any feature and/or aspect discussed above in connections with the compounds according to the invention apply by analogy to the methods described herein.

The following figures and examples are provided below to illustrate the present invention. They are intended to be illustrative and are not to be construed as limiting in any way.

EXAMPLES

In the following examples the xenograft model used is a tumor model with intermediary level of PSMA-ligand uptake of typically 10-15% of injected dose per gram (% ID/g) in mouse xenografts with $^{177}$Lu-PSMA-617 as opposes to the PC3 PIP model used by other researchers which shows an uptake of typically 30-40% ID/g in mouse xenografts.

Example 1. Novel PSMA-Binding Chelator Ligands Compared with PSMA-617

Background: Several carrier molecules for radioligand targeting of prostate specific membrane antigen (PSMA) exists. Lutetium-177 labeled PSMA-617 ($^{177}$Lu-PSMA-617) is the compound in most advanced clinical development stage for use in radionuclide therapy. This molecule works well and give relevant tumor to normal tissue ratios for longer lived (i.e., a half-life of a few days) radionuclides, including $^{177}$Lu and $^{225}$Ac, but at early times points (typically a few hours after injection) shows high uptake in kidneys. With shorter lived radionuclides like $^{212}$Pb (half-life of 10.6 hours), the initial kidney uptake represents a potential toxicity problem. It is therefore advantageous to use a PSMA-ligand with less kidney uptake, but this should not compromise the tumor uptake. The PSMA ligand molecules are made up of (1) a PSMA-binding region, (2) a linker region and (3) a chelator, whereby the linker region connects the (1) and (3). The linker region also is used to adjust molecular size and polarity to affect the in vivo distribution properties. The PSMA-binding region (motif) used in PSMA-617 is a structure that can be found in several molecules of this class developed by several different inventors and researchers including PSMA-11 and PSMA I&T as well as $^{131}$I- and $^{211}$At-labelled PSMA binding ligands.

As can be seen, the p-SCN-Bn-TCMC-PSMA ligand 1 has an extended linker region including a isothiocyanato-benzyl linker and also uses a carbon substituted chelator with all 4 chelator arms free as opposed to PSMA-617 which has a shorter linker region and uses one of the chelator arms as linker attachment. It is shown in later examples herein that these differences cause a significant different biodistribution of the radiolabelled product, making p-SCN-Bn-TCMC-PSMA ligand 1 it more suitable for targeting of $^{212}$Pb to PSMA-expressing tumors, as it reduces kidney exposure compared to PSMA-617.

Materials and methods: The PSMA-ligand precursors for radiolabeling were synthesized by a subcontractor commercial synthesis laboratory.

PSMA-617 was synthesized according to procedures described in the literature. The p-SCN-Bn-TCMC precursors were synthesized according to procedures described in the literature. In the final synthesis step the TCMC-PSMA ligand was synthesized by conjugating p-SCN-Bn-TCMC to amino group of a PSMA binding ligand intermediate. PSMA-617 and TCMC-Bn-PSMA-ligand 1 were both purified by HPLC to a purity of >98% and dried and stored as the trifluoroacetic acid salts. Structures and molecule weights were determined with $^1$H-NMR and MS analysis.

The p-SCN-Bn-TCMC-PSMA ligand 1 trifluoracetic acid salt has the chemical formula $C_{65}H_{86}F_{12}N_{14}O_{21}S$ and a molecular weight of 1659.52 g/mol.

Chemical Name (IUPAC): (((1S)-1-carboxy-5-((2S)-3-(naphthalen-2-yl)-2-((1r,4S)-4-((3-(4-((1,4,7,10-tetrakis(2-amino-2-oxoethyl)-1,4,7,10-tetraazacyclododecan-2-yl)methyl)phenyl)thioureido)methyl)cyclohexane-1-carboxamido)propanamido)pentyl)carbamoyl)-L-glutamic acid; trifloroacetic acid (1:4) The PSMA-617 trifluoroacetic acid salt has the chemical formula $C_{57}H_{75}F_{12}N_9O_{24}$ and a molecular weight of 1498.25 g/mol.

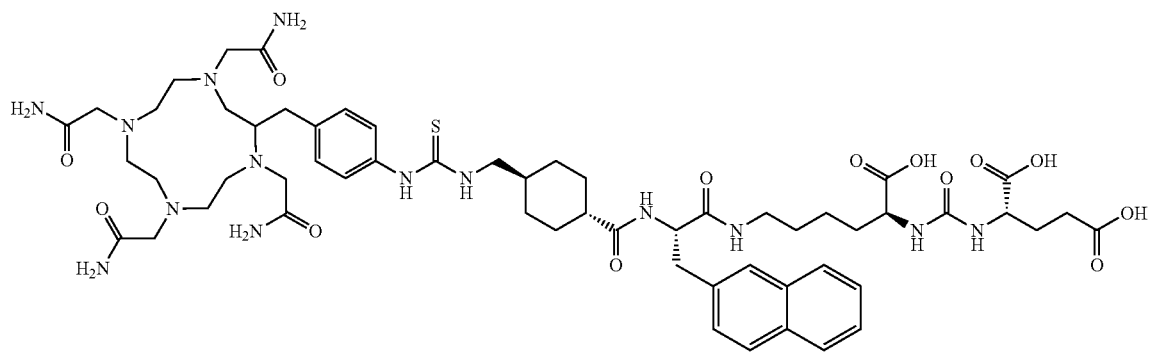

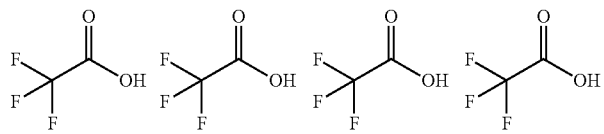

p-SCN-Bn-TCMC-PSMA Ligand 1 Trifluoracetic Acid Salt

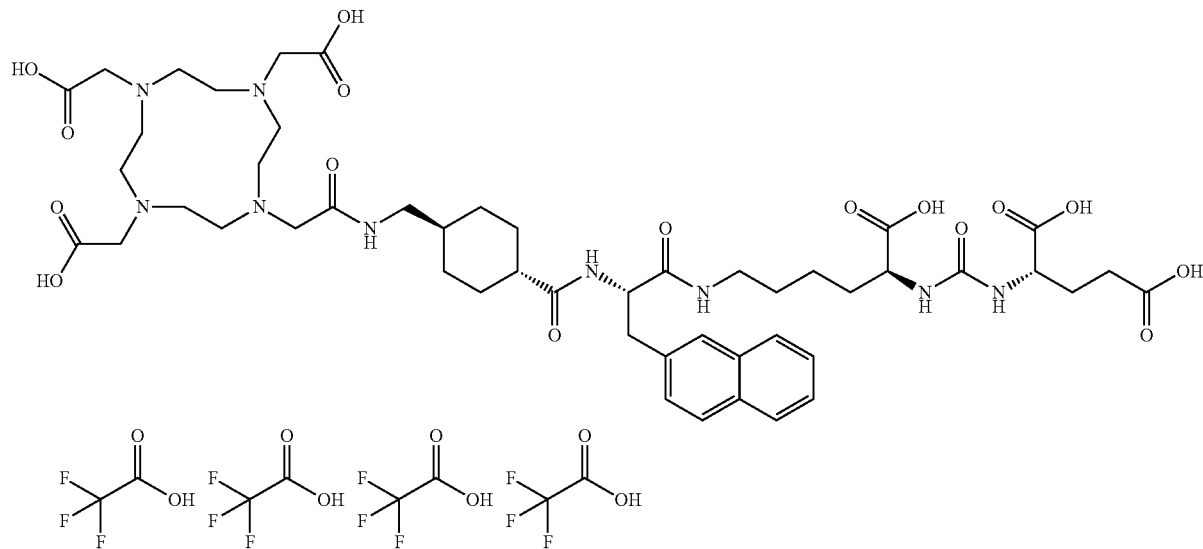

PSMA-617 Trifluoroacetic Acid Salt

As can be seen, the p-SCN-Bn-TCMC-PSMA ligand 1 has an extended linker region including a benzyl linker and also uses a carbon substituted chelator with all 4 chelator arms free as opposed to PSMA-617 which has a shorter linker region and uses one of the chelator arms as linker attachment. It is shown in the following examples that these chemical differences cause a significant different biodistribution of the radiolabelled product, making it more suitable for targeting of $^{212}$Pb to PSMA-expressing tumors, as it reduces kidney exposure compared to PSMA-617.

In conclusion, a novel molecule with same PSMA-binding region, but with different linker region and different chelation properties compared with PSMA-617 is described.

Example 2

A carbon substituted p-SCN-Bn-DOTA-PSMA ligand 2 for radiolabeling with $^{212}$Pb, $^{212}$Bi, $^{213}$Bi, $^{225}$Ac, $^{227}$Th, $^{177}$Lu, etc.

Compared to PSMA-617 the ligand has larger size and a p-SCN-Bn-DOTA group, i.e., both a different linker region and a different DOTA-chelator version where all four chelator arms are free to cause chelation of radionuclides as compared to PSMA-617.

The p-SCN-Bn-DOTA-PSMA ligand 2 is the DOTA analogue of p-SCN-Bn-TCMC-PSMA ligand 1 described in example 1 and has carbon linker to the chelator backbone leaving the chelator groups free to interact with the radiolabel and is therefore expected to improve chelate stability after radionuclide labelling compared with radiolabelled PSMA-617. Due to the additional lipophilic benzyl unit in the linker region and larger size of molecule, less kidney uptake is expected compared with PSMA-617. This molecule can be synthesized in the same fashion as p-SCN-Bn-TCMC-PSMA ligand 1 by using a DOTA based precursor instead of a TCMC-based precursor in the last step of synthesis.

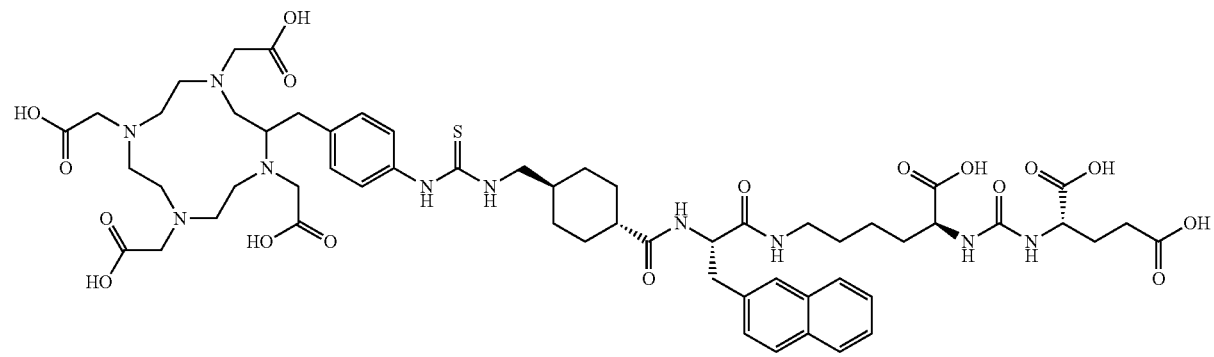

-continued

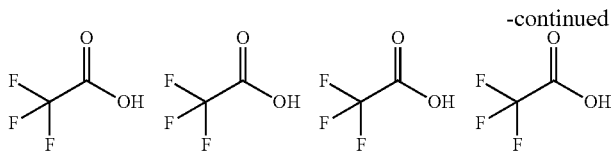

p-SCN-Bn-DOTA-PSMA Ligand 2 Trifluoracetic Acid Salt

The p-SCN-Bn-DOTA-PSMA ligand 2 trifluoracetic acid salt has the chemical formula $C_{65}H_{82}F_{12}N_{10}O_{25}S$ and a molecular weight of 1663.46 g/mol.

With the carbons substituted attachment to the DOTA, this molecule has properties very suitable for radiolabeling with $^{212}$Pb, $^{212}$Bi, $^{213}$Bi, $^{225}$Ac, $^{227}$Th, and also for positron emission tomography (PET) compatible radionuclides like, $^{68}$Ga, as well.

Thus, a novel PSMA-binding molecule is described, p-SCN-Bn-DOTA-PSMA ligand 2, suitable for radioligand imaging and therapy.

In conclusion, carbon substituted p-SCN-Bn-DOTA-PSMA ligand 2 is described with different properties in terms of size and chelation properties compared with PSMA-617.

Example 3. Radionuclides Tested

Lutetium-177 was purchased as ready to use $^{177}$LuCl$_3$ dissolved in diluted HCl. Lead-212 was obtained from $^{224}$Ra based solutions. Radium-224 was made from $^{228}$Th bound to Actinide resin (Eichrom Technologies, LLC) by eluting a column containing actinide resin with immobilized $^{22}$Th with 1 M HCl. The eluate was purified on a second Ac-resin column and the eluate evaporated to dryness using an evaporation vial with a cap with gas inlet and outlet placed in a heater block at approximately 110° C. and a gentle stream of nitrogen gas to evaporate the solvent. When the evaporation vial was empty from solvent it was added 0.1 M HCl to dissolve the residue, typically 200-400 µl.

Example 4. Radiolabeling of PSMA-Binding Ligands

In general, $^{177}$Lu and $^{224}$Ra/$^{212}$Pb solutions were adjusted with HCl with 10% 5 M ammonium acetate to the desired volume and pH 5-6. The PSMA-binding ligands were dissolved in 0.1 M HCl with 0.5 M ammonium acetate to a concentration of 1 mg/ml. Typically a concentration of 20 microgram per 1 ml radioactive solution were used. The reaction mixture was incubated on a shaker for 15-30 minutes, typically a labelling was evaluated by thin layer chromatography. Lead-212 labeling was performed at room temperature or 37° C. with the p-SCN-Bn-TCMC-PSMA ligand 1, while $^{177}$Lu-labeling and $^{212}$Pb-labeling of PSMA-617 was performed at 90° C. Typical radiolabeling yields were in the range 90-100% with the compounds and the radionuclides tested, providing a concentration of 1 µg per 20 µl or higher were used. In conclusion, radiolabeling of both ligands worked well. The novel p-SCN-Bn-TCMC-PSMA ligand 1 could be radiolabelled with $^{212}$Pb at room temperature as opposed to $^{177}$Lu-PSMA-617 that had to be labeled at elevated temperature.

Example 5: Thin Layer Chromatography Analyses

Thin layer chromatography (TLC) was performed using chromatography strips (model #150-772, Biodex Medical Systems Inc, Shirley, N.Y., USA). A formulation buffer (FB) consisting of 7.5% human serum albumin and 5 mM EDTA in DPBS and adjusted to approximately pH 7 with NaOH was mixed with the antibody conjugates in ratio 2:1 for at least 5 minutes before application to the strips to determine free radionuclide. A small beaker with about 0.5 ml of 0.9% NaCl was used to place strips with a sample spot in. To the strip was typically added 1-4 µl of sample at approximately 10% above the bottom of the strip. After the solvent front had moved to about 20% from the top of the strip, the strip was cut in half and each half was placed in a 5 ml test tube for counting. In this system radiolabeled ligand stays at the bottom half while radionuclide complexed with EDTA migrates to the upper half. It was verified that free cations of both $^{212}$Pb and $^{177}$Lu would complex with EDTA and moved to the top. In conclusion, a TLC system was used allowing a rapid determination of radiolabeling yield that would distinguish effectively between radioligand and free radionuclide.

Example 6. Separation of $^{212}$Pb from $^{224}$Ra Solutions

Radiolabeled ligand can be used as a component in $^{224}$Ra dual targeting solutions whereby $^{224}$Ra targets skeletal disease and ligand targets systemic metastatic disease. Alternatively, $^{224}$Ra generator solutions can be used for producing $^{212}$Pb-labeled ligand by labelling in situ, i.e., $^{212}$Pb is complexed by the ligand in the presence of $^{224}$Ra. To 40 µl Radium-224/$^{212}$Pb solutions in 0.5 M ammonium acetate, pH 5-6 was added 2 µl (1 µg/µl) of either p-SCN-Bn-TCMC-PSMA ligand 1 or PSMA-617 and reacted as described to generate the $^{212}$Pb-labeled ligands. To purify $^{212}$Pb-PSMA ligand the product was added about 10 µl of a formulation buffer consisting of 7% bovine serum albumin, 10 mM EDTA, and 10 mg/ml ascorbic acid. Thereafter the reaction mixture was added to a Sephadex G-10 column PD Mini-Trap G-10 (GE Healthcare Life Sciences) and eluted with 0.9% NaCl. The eluate containing the $^{212}$Pb, typically the fractions eluted after application of 0.7-1.5 ml, was collected and analysed on a gamma counter and TLC and radioligand binding assay was performed. The product purification procedure had high radiochemical yield (typically >80%) and had a high radiochemical purity with $^{224}$Ra amounting to less than 0.4% compared with $^{212}$Pb-labeled ligand, typically.

In conclusion, p-SCN-Bn-TCMC-PSMA ligand 1 and PSMA-617 could be radiolabelled with $^{212}$Pb in the presence of $^{224}$Ra yielding a dual targeting solution for combined bone metastases targeting with $^{224}$Ra and systemic tumor cell targeting with $^{212}$Pb-labeled PSMA ligand.

It was also found that using Sephadex G-10 gel filtration column, both $^{212}$Pb-labeled PSMA-ligands tested could be separated from $^{224}$Ra in the solution with a recovery above 80% and breakthrough of $^{224}$Ra of less than 0.4% yielding a highly purified $^{212}$Pb-labeled PSMA radioligand for stand-alone PSMA targeting.

Example 7. Stability Testing of $^{212}$Pb-Labeled Ligands In Vitro

Radiolabeled ligand in $^{224}$Ra/$^{212}$Pb solution was mixed 1:1 with PBS or bovine serum albumin and incubated at 37° C. for up to 48 hours. TLC analyses were performed at 1 h, 4 h, 24 h and 48 h of incubation.

The data are shown in table 1 and indicates that $^{212}$Pb continuously, after it is generated from $^{224}$Ra, react with the ligand and maintain a high percentage of radiochemical purity even after 48 hours. Thus, the PSMA-ligands are compatible with the use of a $^{224}$Ra solution for in situ production of radioligand that is suitable for centralized production and shipment to the end user.

TABLE 1

Radiochemical purity of $^{212}$Pb-TCMC-PSMA ligand 1 and $^{212}$Pb-PSMA-617 in PBS and FBS

| Time since start of incubation | $^{212}$Pb-p-SCN-Bn-TCMC-PSMA ligand 1 | | $^{212}$Pb-PSMA-617 | |
|---|---|---|---|---|
| | PBS | FBS | PBS | FBS |
| 1 h | 93.26% | 93.50% | 91.62% | 92.13% |
| 4 h | 95.04% | 94.18% | 94.33% | 94.37% |
| 24 h | 95.00% | 93.54% | 93.26% | 94.54% |
| 48 h | 95.11% | 90.81% | 93.17% | 95.65% |

Conclusion: The data indicate that p-SCN-Bn-TCMC-PSMA ligand 1 and PSMA-617 labelled with $^{212}$Pb are stable in $^{224}$Ra solutions for a prolonged period of time indicating compatibility with centralized production and shipment to the end user of ready to use product. Such solutions could be used for treatment against cancer.

Example 8. Prostate Cancer Cell Binding of p-SCN-Bn-TCMC-PSMA Ligand 1 and PSMA-617 Labeled with $^{212}$Pb The cell binding fractions measured by adding about 1 ng of radioligand to 0.2 ml of C4-2 cells (5×10$^7$ cells per ml) in a 5 ml test tube and incubate for 1 h before measuring applied activity, wash cells 3 times with 0.5 ml 0.5% bovine serum albumin in DPBS and thereafter recount the washed cell pellet. From multiple experiments it was found that the % bound was in the range of 40-53% after subtracting for nonspecific binding. Nonspecific binding was measured by blocking the cells with excess 10 µg/ml of unlabelled ligand before adding radioligand. No significant difference in cell-binding was found between radiolabelled p-SCN-Bn-TCMC-PSMA ligand 1 and PSMA-617. In conclusion, the radioligand of radiolabelled p-SCN-Bn-TCMC-PSMA ligand 1 and PSMA-617 had similar cell binding properties in vitro indicating that p-SCN-Bn-TCMC-PSMA ligand 1 has relevant antigen binding ability.

Example 9. Radiolytic Stability of p-SCN-Bn-TCMC-PSMA Ligand 1 Assessed by Radioligand Binding Ability with Prostate Cancer Cells and TLC Analyses Table 2 shows the cell binding fractions measured by adding about 1 ng of radioligand to 0.2 ml of C4-2 cells (5×10$^7$ cells per ml) in a 5 ml test tube and incubate for 1 h before measuring applied activity, wash cells 3 times with 0.5 ml 0.5% bovine serum albumin in DPBS and thereafter recount the washed cell pellet. Initial activity in the solution was about 5 MBq/ml causing an absorbed radiation dose to the solution of about 1.8 Gy after 24 h and 3.3 Gy after 48 hours. The data (Table 2) indicate a slight decline at the longest exposure time but in general a relatively strong radiolytic resistance of the ligand was observed, which is compatible with centralized production and shipment to the end user $^{224}$Ra-based generator solution with or without removal of $^{224}$Ra prior to the administration of product.

TABLE 2

Binding ability of $^{212}$Pb-p-SCN-Bn-TCMC-PSMA ligand 1 when kept in $^{224}$Ra solution.

| Time since start of incubation | Cell binding fraction | TLC measured RCP |
|---|---|---|
| 0.5 h | | 93.81% |
| 1 h | | 92.84% |
| 4 h | 52.3% | 94.75% |
| 24 h | 48.16% | 94.85% |
| 48 h | 37.18% | 94.85% |

Conclusion: The data indicate that $^{212}$Pb-p-SCN-Bn-TCMC-PSMA ligand 1 is stable in $^{224}$Ra solutions for a prolonged period of time and the PSMA-ligand is capable of complexing $^{212}$Pb as it is generated from $^{224}$Ra during storage, and provided that the absorbed radiation dose is kept below about 2 kGy such solutions could be used for treatment against cancer.

Example 10. Biodistribution of Radiolabelled Ligands in Nude Mice with C4-2 PSMA-Positive Xenografts The biodistribution of $^{224}$Ra/$^{212}$Pb solutions with p-SCN-Bn-TCMC-PSMA ligand 1 and PSMA-617 labeled with $^{212}$Pb and $^{177}$Lu were compared after intravenous injection in nude mice with C4-2 xenografts at various time points after injection. Each group usually consisted of three mice. The $^{212}$Pb labelling was above 92% for the products. The molar concentration of ligand was significantly lower for the $^{177}$Lu-PSMA-617 since much higher level of radionuclide was used with $^{177}$Lu vs. $^{212}$Pb. Approximately 16 kBq of $^{224}$Ra/$^{212}$Pb was injected in each animal, i.e., approximately 0.2 nmol of ligand per mouse. Animals were given anaesthesia and sacrificed by cervical dislocation followed by dissection and harvesting of tissue-, blood- and urine samples. The samples were weighed and counted on a gamma counter.

Example 11. Comparison of Tumor Binding and Kidney Uptake of p-SCN-Bn-TCMC-PSMA Ligand 1 and PSMA-617 Labelled with $^{212}$Pb in Mice The biodistribution of $^{224}$Ra/$^{212}$Pb solutions with p-SCN-Bn-TCMC-PSMA ligand 1 and PSMA-617 labeled with $^{212}$Pb were compared after intravenous injection in nude mice with C4-2 xenografts at 4 h after injection. Three mice in each group. The $^{212}$Pb labelling was above 92% for both products. The molar concentration was the same for both products, i.e., 12.5 nmol per MBq. Approximately 16 kBq of $^{224}$Ra/$^{212}$Pb was injected in each animal, i.e., approximately 0.2 nmol of ligand per mouse. Animals were given anaesthesia and sacrificed by cervical dislocation followed by dissection and harvesting of tissue-, blood- and urine samples. The samples were weighed and counted on a gamma counter. Results: Four hours after injection, the $^{212}$Pb-p-SCN-Bn-TCMC-PSMA ligand 1 to PSMA-617 ratios were as follows: tumor 1.35; kidneys 0.20; blood 1.21; liver 2.67; spleen 0.71. It was confirmed by counting samples after 3 days storage that the $^{224}$Ra biodistribution was not significantly altered by either of the PSMA-directed ligands. Discussion: $^{212}$Pb p-SCN-Bn-TCMC-PSMA ligand 1 showed a significant different biodistribution compared to $^{212}$Pb-PSMA-617 and especially noteworthy is the very low, and favourable ratio for uptake in the kidneys as kidneys are expected to be the main dose limiting normal tissue related to PSMA radioligand therapy with relatively short-lived alpha-emitters (FIG. 1). In conclusion, $^{212}$Pb-p-SCN-Bn-TCMC-PSMA ligand 1 shows very promising early time point biodistribution compared with PSMA-617 which is important when using shorter lived radionuclides like $^{212}$Pb.

Example 12. Comparison of Tumor Binding and Kidney Uptake of $^{212}$Pb-Labeled p-SCN-Bn-TCMC-PSMA Ligand 1 and $^{177}$Lu-Labeled PSMA-617 in Mice Methods: Tumor and kidney uptake of $^{212}$Pb-labeled p-SCN-Bn-TCMC-PSMA ligand 1 and $^{177}$Lu-labeled PSMA-617 was compared at 1 hours and 4 hours after administration of the products by intravenous injection into nude mice with C4-2 xenografts as described in Example 9. Results: The tumors and the kidneys were the tissues taking up the largest amounts of radioactivity. As examples the tumor and kidney uptake of $^{212}$Pb-p-SCN-Bn-TCMC-PSMA were on average 13.9 and 8.1 percent of injected dose per gram (% ID/g) respectively at 4 hours after injection. The tumor and kidney uptake of $^{177}$Lu-PSMA-617 were on average 13.6 and 17.4% ID/g respectively 4 hours after injection. It is noteworthy that the molar amount of ligand injected was much lower for PSMA-617, which is known to reduce kidney uptake, but still the novel $^{212}$Pb-labeled compound showed less kidney uptake. The tumor-to-kidney ratios at the 4-hour timepoint were as follows: $^{212}$Pb-p-SCN-Bn-TCMC-PSMA ligand 1, 1.7; $^{177}$Lu-PSMA-617, 0.8.

The average tumor-to-kidney ratios determined at the 1-hour point after administration were for $^{212}$Pb-p-SCN-Bn-TCMC-PSMA ligand 1, 0.40 and for $^{177}$Lu-PSMA-617, 0.17. In conclusion, despite a higher molar ligand concentration for $^{212}$Pb-p-SCN-Bn-TCMC-PSMA ligand 1, it showed better tumor to kidney ratios than $^{177}$Lu-PSMA-617 indicating that it may be well suited for $^{212}$Pb based alpha emitter radioligand therapy.

Example 13. Biodistribution of Single Targeting Solution Containing $^{212}$Pb-p-SCN-Bn-TCMC-PSMA Ligand 1 in Mice with PSMA-Positive Xenografts Using a $^{212}$Pb/$^{224}$Ra solution for reaction with p-SCN-Bn-TCMC-PSMA ligand 1 as described, purified $^{212}$Pb-p-SCN-Bn-TCMC-PSMA ligand 1 was purified using a Sephadex G-10 gel filtration column and about 30 kBq and 300 ng of the purified radioligand product was injected per animal. The data are shown in Table 3. As can be seen the kidney activity is reduced relatively quickly, while the tumor uptake shows good retention. The tumor-to-tissue ratios (Table 4) indicates suitability for radioligand targeting with $^{212}$Pb.

In conclusion, $^{212}$Pb-p-SCN-Bn-TCMC-PSMA ligand 1 shows relevant targeting properties for use in radioligand therapy against PSMA-expressing prostate cancer.

TABLE 3

Biodistribution for $^{212}$Pb-p-SCN-Bn-TCMC-PSMA ligand 1 at various timepoints post injection

| Organ | % ID/g | | | |
|---|---|---|---|---|
| | 1 h | 2 h | 4 h | 8 h |
| Blood | 1.77 | 0.54 | 0.46 | 0.13 |
| Urine | 253.36 | 250.85 | 32.12 | 6.76 |
| Testes | 4.41 | 0.56 | 0.38 | 0.12 |
| Prostate | 13.95 | 3.80 | 1.48 | −0.10 |
| Salivary gland | 0.72 | 0.32 | 0.34 | 0.15 |
| Tumor | 26.44 | 15.87 | 14.14 | 14.65 |
| Skin | 1.70 | 0.47 | 0.42 | 0.23 |
| Kidneys | 63.96 | 25.41 | 9.19 | 4.07 |
| Liver | 2.39 | 1.33 | 1.55 | 1.25 |
| Spleen | 1.24 | 0.44 | 0.54 | 0.36 |
| Small intestine | 0.34 | 0.23 | 0.30 | 0.08 |
| Large intestine | 0.25 | 0.39 | 0.18 | 0.17 |
| Stomach | 0.16 | 0.22 | 0.10 | 0.09 |
| Lungs | 1.19 | 0.40 | 0.75 | 0.17 |
| Heart | 0.78 | 0.20 | 0.52 | 0.09 |
| Bladder | 36.86 | 6.85 | 3.53 | 0.26 |
| Femur | 0.87 | 0.40 | 0.57 | 0.74 |
| Muscle | 0.62 | 0.22 | 0.23 | 0.04 |
| Brain | 0.61 | 0.04 | 0.07 | 0.02 |
| Skull | 0.77 | 0.38 | 0.37 | 0.63 |

TABLE 4

Tumor to tissue ratios for $^{212}$Pb-p-SCN-Bn-TCMC-PSMA ligand 1 at various timepoints

| | 1 h | 2 h | 4 h | 8 h |
|---|---|---|---|---|
| Tumor/blood | 14.9 | 29.4 | 30.7 | 112.7 |
| Tumor/kidneys | 0.41 | 0.62 | 1.54 | 3.60 |
| Tumor/muscle | 42.6 | 72.1 | 61.5 | 366.2 |
| Tumor/Femur | 30.4 | 39.7 | 24.8 | 19.8 |

Example 14—Dosage

The radiation energy produced for the two nuclides is mainly from alpha particles and therefore only the alpha particles are considered in the following estimate.

The $^{212}$Pb and short-lived daughters produce on average 7.8 MeV alpha radiation per atom of $^{212}$Pb. The half-life of $^{212}$Pb is 10.6 h.

The $^{213}$Bi and short-lived daughters produce on average 8.4 MeV of alpha energy per atom of $^{213}$Bi. The half-life of $^{213}$Bi is 46 min.

It is assumed an equivalent dose for alpha particles of 5 Sv/Gy.

Thus 1 Bq of $^{212}$Pb produce an equivalent alpha dose of 1×(10.6×60/46)×7.8/8.4=12.6 Bq of $^{213}$Bi when decaying completely.

It has been reported that salivary glands, kidneys and red marrow are the dose limiting tissues for $^{213}$Bi and $^{225}$Ac complexed to PSMA-617 (Kratochwil, et al, 2018).

Based on the imaging of PSMA-617 labeled with radionuclides suitable for positron emission tomography detection, it is assumed a maximum percentage uptake to be at the 30 minutes time point, that 70% $^{213}$Bi atoms relative to 90% of $^{212}$Pb would reach and decay in tumors (i.e., the relative decay fraction).

The relative decay fraction for the dose limiting tissues is assumed to be 70% for all the tissues with $^{213}$Bi-PSMA-617. For $^{212}$Pb-PSMA-617 taken up it is assumed that 50% would decay in the salivary glands, 30% in kidneys and 20% in bone marrow.

By correcting for energy per Bq and the relative decay fraction for $^{212}$Pb- and $^{213}$Bi-labeled PSMA-617 the dose estimate for $^{212}$Pb-PSMA-617 would be as presented in Table 5 together with previously published data for $^{213}$Bi- and $^{225}$Ac-labeled PSMA-617. Also, by using mouse data comparison of $^{212}$Pb-p-SCN-Bn-TCMC-PSMA ligand 1 and $^{212}$Pb-PSMA-617 and assuming similar tissue uptake ratio in man dosimetry estimate for $^{212}$Pb-p-SCN-Bn-TCMC-PSMA ligand 1 is presented in Table 5.

TABLE 5

Dose assessment assuming similar stability and affinity of products regardless of radionuclide.

| Organ | $^{225}$Ac-PSMA-617$^a$ Sv/MBq | $^{213}$Bi-PSMA-617$^b$ Sv/GBq | $^{212}$Pb-PSMA-617 Sv/100 MBq | $^{212}$Pb-p-SCN-Bn-TCMC-PSMA ligand 1 Sv/100 MBq$^c$ |
|---|---|---|---|---|
| Salivary glands | 2.33 | 8.1 | 5.67 | 5.67 |
| Kidneys | 0.74 | 8.1 | 3.40 | 1.70 |
| Red marrow | 0.05 | 0.52 | 0.19 | 0.19 |
| Tumors | 5.7 | 6.3 | 10.2 | 10.2 |

$^a$From Kratochwil et al 2017.
$^b$From Kratochwil et al 2018.
$^c$Assuming same uptake as for $^{212}$Pb-PSMA-617 exept for kidneys which is assumed to be reduced by 50%.

It has been reported that both $^{225}$Ac- and $^{213}$Bi-labeled PSMA-617 has been used clinically and shown considerable antitumor activity. Based on the estimates in this example it is indicated that $^{212}$Pb-labeled urea based PSMA inhibitor is a very promising therapeutic tool against PSMA expressing cancer.

Example 15 Dosimetry Estimate for Dual Targeting $^{224}$Ra Cation and $^{212}$Pb-Labeled PSMA Targeting Urea Derivative Using $^{224}$Ra in equilibrium with $^{212}$Pb-labeled PSMA binding urea derivative.

For a dosage of 150 kBq of $^{224}$Ra the total activity administered would be 10.5 MBq in a 70 kg person. By using published dosimetry for cationic $^{223}$Ra in prostate cancer patient and correcting for half-life difference between $^{224}$Ra and $^{223}$Ra, assuming same biodistribution, and considering the different residence times in the various tissues it was found that $^{224}$Ra would give per MBq administered 0.006 Gy to kidneys, 0.029 Gy to salivary glands, 0.26 Gy to red marrow and anr estimated 5 times the red marrow uptake to tumors i.e, 1.3 Gy.

An equivalent dose of 5 Sv/Gy for alpha particle dose is assumed and the data is translated to Sv per injected dosage (10.5 MBq/pasient) in Table 6.

TABLE 6

Dose assessment of $^{224}$Ra cation + $^{212}$Pb-labeled PSMA binding urea derivative*.

| Organ | $^{224}$Ra$^a$ Sv/10.5 MBq | $^{212}$Pb-p-SCN-Bn-TCMC-PSMA ligand 1 Sv/10.5 MBq$^c$ | $^{224}$Ra cation + $^{212}$Pb-p-SCN-Bn-TCMC-PSMA ligand 1 Sv/10.5 MBq |
|---|---|---|---|
| Salivary glands | 37 | 0.60 | 0.97 |
| Kidneys | 0.39 | 0.36 | 1.7 |

TABLE 6-continued

Dose assessment of $^{224}$Ra cation + $^{212}$Pb-labeled PSMA binding urea derivative*.

| Organ | $^{224}$Ra$^a$ Sv/10.5 MBq | $^{212}$Pb-p-SCN-Bn-TCMC-PSMA ligand 1 Sv/10.5 MBq$^c$ | $^{224}$Ra cation + $^{212}$Pb-p-SCN-Bn-TCMC-PSMA ligand 1 Sv/10.5 MBq |
|---|---|---|---|
| Red marrow$^b$ | 2.2 | 0.02 | 2.22 |
| Tumors (bone metastases/soft tissue metastases) | 10.5/0.09 | 1.07/1.07 | 11.6/1.16 |

*Assuming 1:1 ratio between $^{224}$Ra and $^{212}$Pb.
$^a$From Lassmann et al, 2002.
$^b$It should be noted that the red marrow is mainly irradiated from bone surface deposits of Ra, and due to short range of alpha-particles from the bone surfaces, substantial areas of red bone marrow are outside of reach from bone surface alpha particles. Equivalent dose of 5 for alpha-particle dose is assumed.

Example 15. Dosimetry Estimated for $^{227}$Th-Labeled PSMA Binding Urea Derivative In this example the $^{177}$Lu is assumed labeled to p-SCN-Bn-DOTA-PSMA ligand 2 or a HOPO derived version of this molecule. The current estimates are based on adaptations of data from studies of $^{223}$Ra in patients and $^{225}$Ac-PSMA-617 in patients with prostate cancer (Chittenden et al., 2015, Kratochwil et al, 2017, 2018).

An equivalent dose of 5 Sv per Gy is assumed for the alpha particle radiation.

It is assumed that the $^{223}$Ra generated in tissues would decay locally. It is assumed that 40% of the $^{223}$Ra generated from whole body circulation of $^{227}$Th is retained in the skeleton. Only the alpha particle dose is considered as this constitute 95% or more of the total radiation energy produced.

In tissue with a longer residence times for the radiolabeled PSMA urea derivative (salivary gland, kidneys and tumors) the cumulated activity of $^{223}$Ra produced from $^{227}$Th is assumed to be 20% of the $^{227}$Th and for red bone marrow 5%.

The 20% and 5% radium generated from $^{227}$Th in the various tissues are assumed to be in equilibrium with alpha-emitting progeny radionuclides, so each radium decay in effect produces 26.4 MeV of alpha radiation while $^{227}$Th produces one alpha of 5.9 MeV.

Since residence times are lower than the half-lives of $^{225}$Ac and $^{227}$Th, the cumulated activity for $^{227}$Th is assumed to be only 10% higher than for $^{225}$Ac (not considering $^{225}$Ac progenies) in all organs. It is assumed a total of 27.7 MeV of alpha dose per atom of $^{225}$Ac from decay of the mother nuclide and alpha emitting progenies.

It is also assumed that the red marrow dose and skeletal tumor dose is increased by a factor of 2 vs. the red marrow dose, due to skeletal uptake of $^{223}$Ra generated during systemic circulation etc of the $^{227}$Th-product.

The data are presented in Table 7. The data indicate favorable tumor to tissue ratios for $^{227}$Th-labeled PSMA binding urea derivative.

TABLE 7

Dosimetry estimated of equivalent doses for critical organs and tumors for $^{227}$Th-labeled PSMA binding urea derivative (MBq/patient).

| Organ | $^{227}$Th (Sv/MBq) | $^{223}$Ra (co-localized with $^{227}$Th) | $^{227}$Th + $^{223}$Ra |
|---|---|---|---|
| Salivary glands | 0.55 | 0.49 | 1.04 |
| Kidneys | 0.17 | 0.15 | 0.32 |
| Red marrow | 0.012 | 0.003 | 0.030* |
| Tumors (soft tissue/bone met.) | 1.33/1.33 | 1.19/1.19 | 2.52/2.67* |

*Includes added skeletal dose of $^{223}$Ra generated from $^{227}$Th during circulation phase.

The data in Table 7 represent $^{227}$Th-labeled PSMA binding urea derivative (e.g. PSMA-617) which is purified from $^{223}$Ra prior to injection. Alternatively, it is possible to use the $^{227}$Th-product solution with a presence of various amounts of $^{223}$Ra to increase dose to the bone metastases, e.g., if the bone disease is very dominating compared with soft tissue disease.

It is assumed that the products described herein can be used in single treatment or in repeated treatment fashion.

In conclusion, the dosimeric estimates for PSMA-targeting urea derivatives labeled with $^{212}$Pb or $^{227}$Th indicates promising tumor to tissue ratios indicating that clinical benefit of use may be possible.

Example 16. Comparative Therapy Experiment with $^{177}$Lu-PSMA-617 and $^{212}$Pb-p-SCN-Bn-TCMC-PSMA Ligand 1 in Nude Mice with C4-2 Xenografts Male nude mice were inoculated in the flanks with C4-2 PSMA positive human prostate cells and 2 weeks later when tumors were 5-7 mm in diameters. Groups of 8 animals each received saline, 52 MBq of $^{177}$Lu-PSMA-617 or 320 kBq of $^{212}$Pb-p-SCN-Bn-TCMC-PSMA ligand 1. Animals were sacrificed when tumor size reached 20 mm due to animal welfare requirements. Tumor dosimetry was calculated based on the following assumptions: for $^{177}$Lu-PSMA-617 effective half-life in tumor of 3 days, 10% of injected dose per gram decays in tumor and 80% of radiation from decays in tumors is aborbed in tumors and 0.15 MeV radiation energy per decay. For $^{212}$Pb the effective half-life was assumed to be 10.6 h, 10% of injected dose per gram decays in tumor and 100% of radiation in a tumor is absorbed in the tumor, 100% retention of $^{212}$Pb and daughters in the tumors and 8 MeV radiation energy per decay. The tumor dosimetry for the injected activities gave on average 35.9 Gy to tumors for $^{177}$Lu-PSMA-617 and 2.06 Gy to tumors for $^{212}$Pb-p-SCN-Bn-TCMC-PSMA ligand 1 groups respectively.

Figure 2:
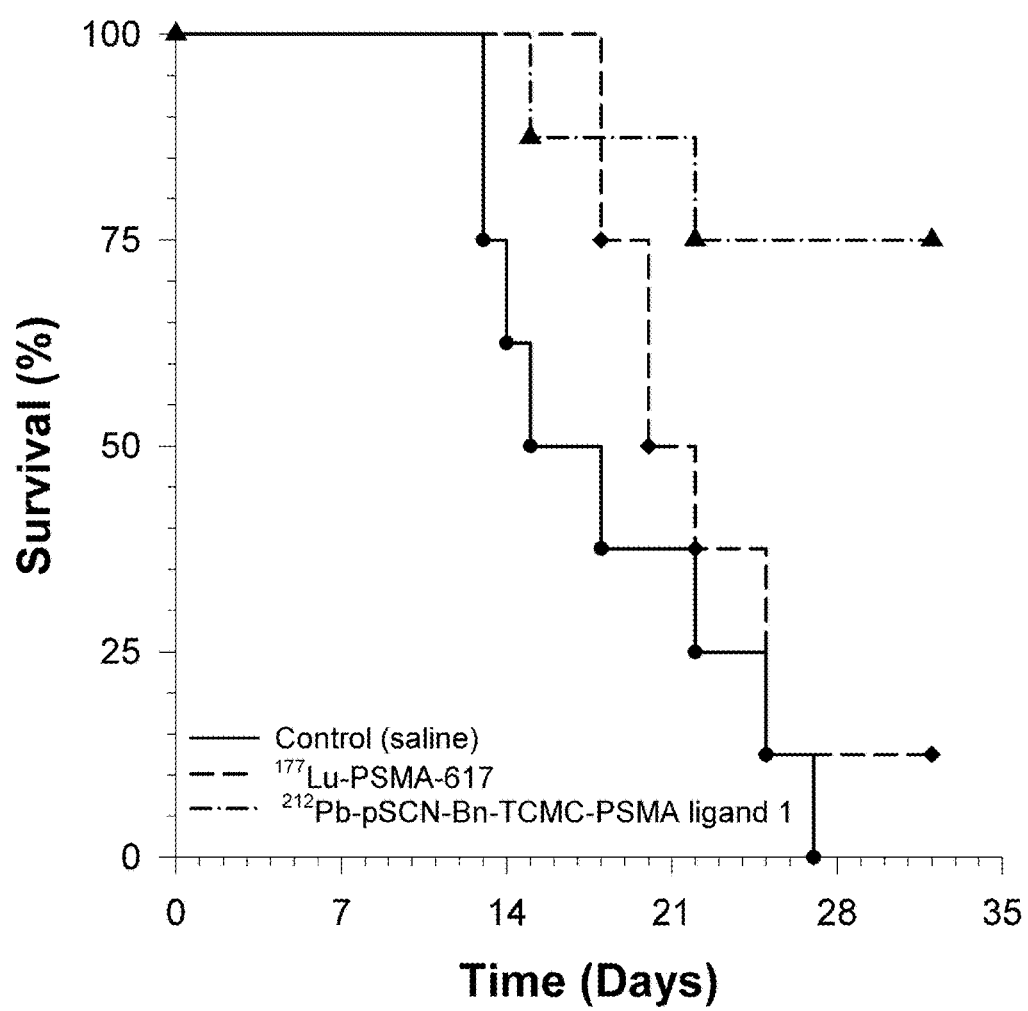
FIG. 2 shows survival of mice with C4-2 PSMA positive xenograft after treatment with saline, 52 MBq $^{177}$Lu-OSMA-617 and 0.32 MBq $^{212}$Pb-p-SCN-Bn-TCMC-PSMA ligand 1.

Results: At day 30 after treatment the following the data showed 0%, 12.5% and 75% survival in the saline, $^{177}$Lu-PSMA-617 and $^{212}$Pb-p-SCN-Bn-TCMC-PSMA ligand 1 groups respectively (FIG. 2). The median survival was 15 days, 20 days and >30 days (not reached) in the saline, $^{177}$Lu-PSMA-617 and $^{212}$Pb-p-SCN-Bn-TCMC-PSMA ligand 1 groups, respectively.

In conclusion, the data indicates a strong tumor growth delay with $^{212}$Pb-p-SCN-Bn-TCMC-PSMA ligand 1 vs $^{177}$Lu-PSMA-617 even though the radiation dose estimates show a 17 times higher radiation dose, in terms of Gy, delivered with $^{177}$Lu-PSMA-617.

Thus, the radiobiological effectiveness (RBE) for $^{212}$Pb-p-SCN-Bn-TCMC-PSMA ligand 1 vs $^{177}$Lu-PSMA-617 was at least 17. This high radiobiological effectiveness for therapeutic levels of alpha emitter was highly unexpected as usually an RBE of 2-5 is expected for alpha emitters vs beta emitters.

REFERENCES

An efficient chelator for complexation of thorium-227. Ramdahl T, Bonge-Hansen H T, Ryan O B, Larsen S, Herstad G, Sandberg M, Bjerke R M, Grant D, Brevik E M, Cuthbertson A S Bioorg Med Chem Lett. 2016 Sep. 1; 26(17):4318-21. In Vitro and In Vivo Efficacy of a Novel CD33-Targeted Thorium-227 Conjugate for the Treatment of Acute Myeloid Leukemia.

Hagemann U B, Wickstroem K, Wang E, Shea A O, Sponheim K, Karlsson J, Bjerke R M, Ryan O B, Cuthbertson A S Mol Cancer Ther. 2016 October; 15(10):2422-2431.

Chittenden S J., A phase 1, open-label study of the biodistribution, pharmacokinetics, and dosimetry of 223Radicloride in patinets with hormone-refractory prostate cancer and skeletal metastases. J Nucl Med 56: 1304-1309 (2015).

Kratochwil C et al., Targeted α-therapy of metastatic castration resistant prostate cancer with 225Ac-PSMA-617: Dosimetry estimate and empirical dose finding J Nucl Med 58: 1624-1631 (2017).

Kratochwil C et al., Targeted α-therapy of mCRPC: Dosimetry estimate of 213Bismuth-PSMA-617. Eur J Nucl Med Mol Imaging 45:31-37 (2018)

Huang S S, Heston W D W. Should Low Molecular Weight PSMA Targeted Ligands Get Bigger and Use Albumin Ligands for PSMA Targeting? Theranostics 7: (7) 1940-1941 (2017)

Choy C J et al., 177Lu-Labeled Phosphoramidate-Based PSMA Inhibitors: The Effect of an Albumin Binder on Biodistribution and Therapeutic Efficacy in Prostate Tumor-Bearing Mice. Theranostics. 2017; 7(7):1928-1939. doi:10.7150/thno.18719.

Lassmann, M et al., Therapy of ankylosing spondylitis with 224Ra-radium chloride:Dosimetry and risk considerations. Radiat Environ Biophys 41: 173-178 (2002).

ITEMS

1. Compound X, wherein the compound X is a urea derivative suitable for targeting of PSMA expressing cells and tissues.

2. A complex comprising a compound X linked to $^{212}$Pb, $^{177}$Lu, $^{213}$Bi, $^{225}$Ac or $^{227}$Th, wherein the compound X is a urea derivative suitable for targeting of PSMA expressing cells and tissues.

3. The compound of item 1 or the complex according to item 2, wherein the compound X is linked to $^{212}$Pb or $^{227}$Th by a chelating moiety Z.

4. The compound or complex according to any of items 1-3, wherein the chelating moiety Z is selected from the group consisting of acyclic chelators, cyclic chelators, cryptands, crown ethers, porphyrins or cyclic or noncyclic polyphosphonates, DOTMP, EDTMP, bisphosphonate, DOTA, a DOTA derivative such as p-SCN-Bn-DOTA, pamidronate conjugated to DOTA, TCMC, a TCMC derivative such as p-SCN-Bn-TCMC, pamidronate conjugated to TCMC, antibody-conjugated-DOTA, antibody-conjugated-TCMC, HBED-CC, NOTA, NODAGA, TRAP, NOPO, PCTA, DFO, DTPA, CHX-DTPA, AAZTA, DEDPA, and oxo-Do3A.

4. The compound or complex according to any of items 1-4, wherein the linker is DOTA or a DOTA derivative.

5. The compound or complex according to any of items 1-4, wherein the linker is a DOTA derivative such as p-SCN-Bn-DOTA.

6. The compound or complex according to any of items 1-4, wherein the linker is TCMC or a TCMC derivative.

7. The compound or complex according to any of items 1-4 or 6, wherein the linker is a TCMC derivative such as p-SCN-Bn-TCMC.

8. The compound or complex according to any of items 1-7, wherein the linker an octadentate hydroxypyridinone-containing ligand, such as 3,2-HOPO.

9. The compound or complex according to any of items 1-8, wherein compound X linked to a chelating moiety Z is defined by the formula I:

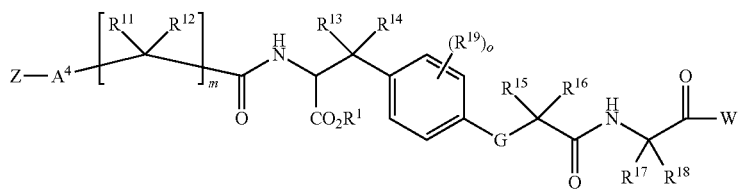

Formula I or a pharmaceutically acceptable salt thereof,
wherein

W is a PSMA-targeting ligand;

$A^4$ is a bond or a divalent linking moiety comprising 1 to 10 carbon atoms in a chain, a ring, or a combination thereof, wherein at least one carbon atom is optionally replaced with O, —$NR^3$—, or —C(O)—;

G is C=O, C=S, C—$NH_2$, or C—$NR^3$;

$R^1$ is hydrogen or a carboxylic acid protecting group;

$R^3$ is selected from the group consisting of hydrogen, alkyl, cycloalkyl, heterocycloalkyl, aryl, alkylaryl, and heteroaryl.

$R^{11}$, $R^{12}$, $R^{13}$, $R^{14}$, $R^{15}$, and $R^{16}$ are each independently hydrogen, alkyl, alkoxyl, or $R^{17}$ and $R^{18}$ are each independently hydrogen, alkyl, aryl, or alkylaryl;

$R^{19}$ is selected from the group consisting of alkyl, alkoxyl, halide, haloalkyl, and CN;

m is an integer from 1 to 6; and o is an integer from 0 to 4, wherein when o is greater than 1, each $R^{19}$ is the same or different.

10. The compound or complex according to any of items 1 to 9, or a pharmaceutically acceptable salt thereof, wherein $A^4$ is a bond, $(CH_2)_n$, —HC(O)—, —$(OCH_2CH_2)_n$—, —$(HCH_2CH_2)_n$—, —H(CO)$CH_2$—, —HC(O)$CH_2$ $(OCH_2CH_2)_n$—, or —HC(O)$CH_2(HCH_2CH_2)_n$—; and L is a bond, $(CH_2)_n$, —$(OCH_2CH_2)_n$—, —(HCH$_2$CH$_2)_n$—, or —C(O)$(CH_2)_n$—;

wherein n is independently 1, 2, or 3.

11. The compound or complex according to any of items 1-10, or a pharmaceutically acceptable salt thereof, wherein $A^4$ is a bond, —$(OCH_2CH_2)_n$—, or —HC(O)$CH_2$ $(OCH_2CH_2)_n$—; and L is a bond, or —$(OCH_2CH_2)_n$—;

wherein n is independently 1 or 2.

12. The compound or complex according to any of items 1-11, or a pharmaceutically acceptable salt thereof, wherein W has the structure:

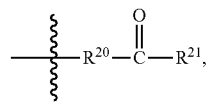

wherein $R^{20}$ and $R^{21}$ are each independently an amino acid residue linked via an amino group thereof to the adjacent —C(O)— group.

13. The compound or complex according to any of items 1-12, or a pharmaceutically acceptable salt thereof, wherein W has the structure:

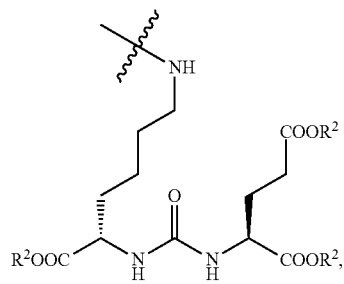

wherein R is hydrogen or a carboxylic acid protecting group.

14. The compound or complex according to any of items 1-13, or a pharmaceutically acceptable salt thereof, having the structure:

or a pharmaceutically acceptable salt thereof,
wherein $R^{17}$ is aryl.

15. The compound or complex according to any of items 1-14, or a pharmaceutically acceptable salt thereof, wherein the complex is PSMA-617:

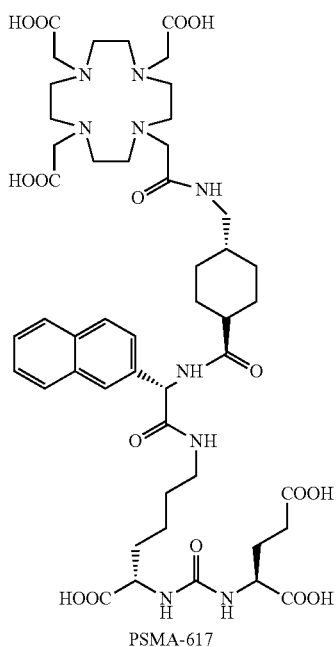

PSMA-617

With the radionuclide, such as $^{212}$Pb, can be linked/chelated to the four N.

16. The compound or complex according to item 15, wherein the DOTA unit is substituted with a TCMC unit.

17. The compound or complex according to items 15-16, wherein DOTA is p-SCN-Bn-DOTA and TCMC is p-SCN-Bn-TCMC.

18. The compound or complex according to items 15-17, wherein p-SCN-Bn-DOTA or p-SCN-Bn-TCMC are backbone C-linked to the urea derivative (PSMA).

19. The compound or complex according to items 15-18, wherein the compound is backbone-C linked p-SCN-Bn-DOTA or p-SCN-Bn-TCMC:

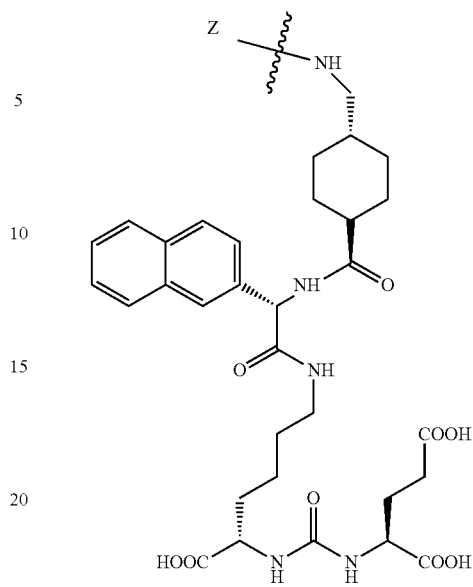

Wherein Z is:

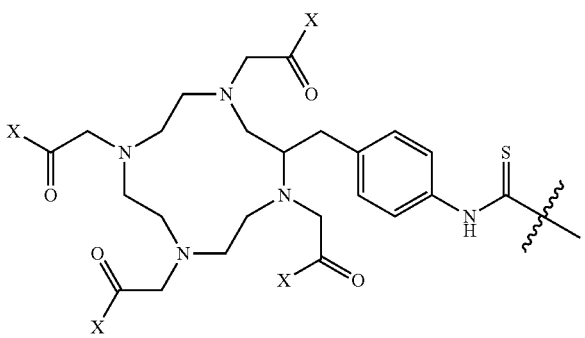

And wherein X is: —OH or NH$_2$.

20. The compound or complex according to items 15-19, wherein the compound is backbone-C linked p-SCN-Bn-DOTA or p-SCN-Bn-TCMC:

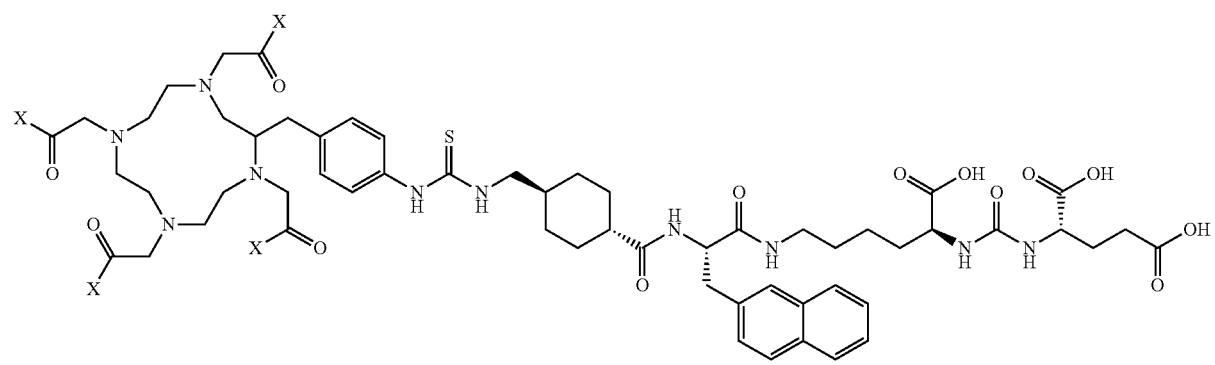

wherein X is: —OH or NH$_2$.

21. The compound or complex according to items 15-20, wherein the compound is backbone-C linked p-SCN-Bn-DOTA i.e. p-SCN-Bn-DOTA-PSMA-ligand 2:

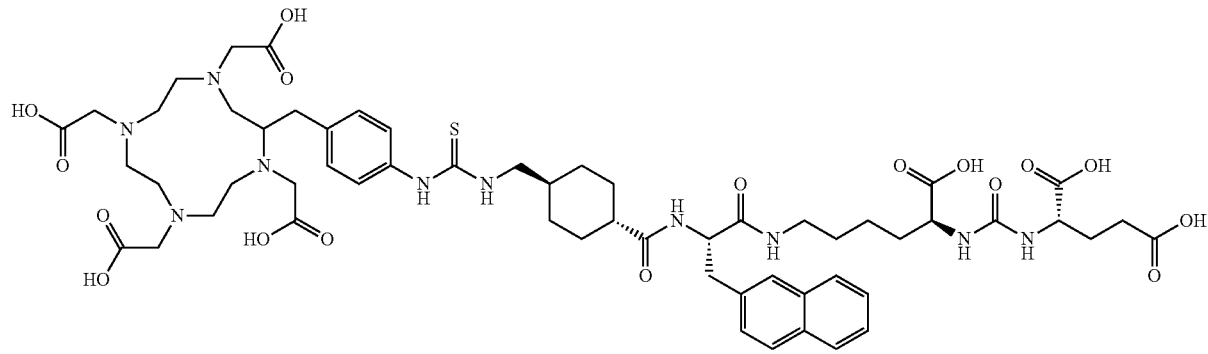 [SMILES: O=C(O)CC[C@H](NC(=O)N[C@@H](CCCCNC(=O)[C@H](Cc1ccc2ccccc2c1)NC(=O)[C@H]1CC[C@H](CNC(=S)Nc2ccc(CC3CN(CC(=O)O)CCN(CC(=O)O)CCN(CC(=O)O)CCN3CC(=O)O)cc2)CC1)C(=O)O)C(=O)O]

22. The compound or complex according to items 15-20, wherein the compound is backbone-C linked p-SCN-Bn-TCMC i.e. p-SCN-Bn-TCMC-PSMA ligand 1:

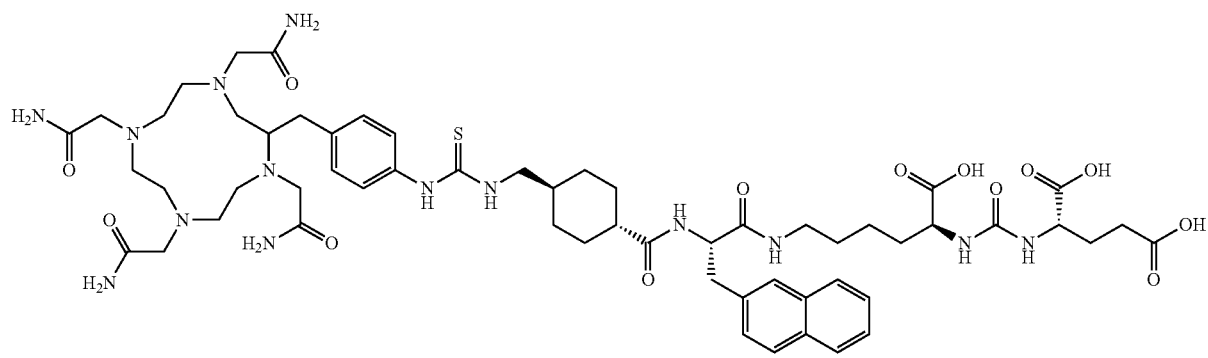 [SMILES: NC(=O)CN1CCN(CC(N)=O)CCN(CC(N)=O)C(Cc2ccc(NC(=S)NC[C@H]3CC[C@H](C(=O)N[C@@H](Cc4ccc5ccccc5c4)C(=O)NCCCC[C@H](NC(=O)N[C@@H](CCC(=O)O)C(=O)O)C(=O)O)CC3)cc2)CN(CC(N)=O)CC1]

23. A PSMA targeting urea derivative containing a TCMC group for chelating $^{212}$Pb.
24. A PSMA targeting urea derivative containing HOPO for chelating $^{227}$Th.
25. A PSMA targeting urea derivative containing DOTA labeled with either $^{212}$Pb or 227Th.
26. A pharmaceutical composition comprising the compound or complex according to items 1-21, and/or a PSMA targeting urea derivative according to claims 15-17, and a diluent, carrier, surfactant, and/or excipient.
27. The radiopharmaceutical composition according to item 26, further comprising $^{224}$Ra.
28. The radiopharmaceutical composition according to any of the items 26-27, wherein the radioactivity is 100 kBq to 100 MBq per done.
29. The radiopharmaceutical composition according to any of items 26-28, wherein the amount of $^{224}$Ra and $^{212}$Pb is in radioactive equilibrium.
30. The radiopharmaceutical composition according to any of items 26-29, wherein the activity ratio (MBq) between $^{212}$Pb to $^{224}$Ra is between 0.5 and 2, such as 0.8-1.5, or such as 0.8-1.3, or preferably such as 0.9-1.15.
31. A kit comprising:
a first vial comprising a radiopharmaceutical composition according to any of items 26-30, and
a second vial comprising a neutralizing solution to adjust pH and/or isotonicity of the radiopharmaceutical composition prior to administration to a patient.

32. A kit comprising:
a first vial comprising a solution comprising $^{224}$Ra, $^{212}$Pb and/or $^{227}$Th;

a second vial comprising a complexing agent selected from the group consisting of acyclic chelators, cyclic chelators, cryptands, crown ethers, porphyrins or cyclic or noncyclic polyphosphonates, DOTMP, EDTMP, bisphosphonate derivatives, DOTA, a DOTA derivative, pamidronate conjugated to DOTA, TCMC, a TCMC derivative, pamidronate conjugated to TCMC, antibody-conjugated-DOTA, antibody-conjugated-TCMC, HBED-CC, NOTA, NODAGA, TRAP, NOPO, PCTA, DFO, DTPA, CHX-DTPA, AAZTA, DEDPA, and oxo-Do3A, or compound according to any of items 1-21, wherein the complexing agent is capable of complexing a daughter nuclide of $^{224}$Ra, such as $^{212}$Pb, and wherein the complexing agent does not complex $^{224}$Ra in the pharmaceutical solution; and
optionally, instructions for mixing the first vial and the second vial, thereby forming a pharmaceutical composition ready to be administered to a patient 1 minute to 12 hours after mixing.
33. The kit according to any of claims 31-32, wherein the kit is for use as a medicament.
34. The radiopharmaceutical composition according to any of items 18-22 for use as a medicament.
35. The radiopharmaceutical composition according to any of items 18-22 for use in the treatment of skeletal disease.
36. The radiopharmaceutical composition for use according to item 35, wherein the skeletal disease is selected from the group consisting of skeletal metastases from cancers to the breast, prostate, kidneys, lung, bone, or multiple myeloma, or non-cancerous diseases causing undesired calcification including ankylosing spondylitis.

37. The radiopharmaceutical composition for use according to any of items 34-36, wherein the solution is administered at a dose in the range 50-150 kBq per kg of bodyweight, such as 50-100 kBq per kg of bodyweight.

38. A method of treatment of malignant or non-malignant disease by administration of a radiopharmaceutical composition as described in items 26-30 to an individual in need thereof.

39. A method for providing a radiopharmaceutical composition according to any of items 26-30, the method comprising:

a) providing a first solution wherein the amount of $^{224}$Ra and $^{212}$Pb is in radioactive equilibrium;

b) providing a second solution comprising a complexing agent that is selected from the group consisting of acyclic chelators, cyclic chelators, cryptands, crown ethers, porphyrins or cyclic or noncyclic polyphosphonates, DOTMP, EDTMP, bisphosphonate, DOTA, a DOTA derivative, pamidronate conjugated to DOTA, TCMC, a TCMC derivative, pamidronate conjugated to TCMC, antibody-conjugated-DOTA, antibody-conjugated-TCMC, HBED-CC, NOTA, NODAGA, TRAP, NOPO, PCTA, DFO, DTPA, CHX-DTPA, AAZTA, DEDPA, and oxo-Do3A, wherein the complexing agent is capable of complexing a daughter nuclide of $^{224}$Ra, such as $^{212}$Pb, and wherein the complexing agent does not complex $^{224}$Ra; and c) mixing the first composition and the second composition, thereby providing a pharmaceutical composition according to any of item 26-30.

The invention claimed is:

1. A compound comprising a prostate specific membrane antigen (PSMA) binding unit and a chelating unit, wherein the PSMA binding unit is carbon-backbone linked to the chelating unit wherein the compound is:

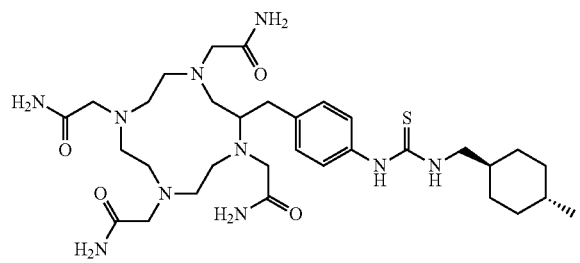

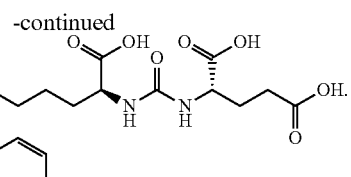

p-SCN-Bn-TCMC-PSMA ligand 1

2. The compound according to claim 1, which is complexed with a radionuclide selected from the group consisting of $^{212}$Pb, $^{212}$Bi, $^{213}$Bi, $^{225}$Ac and $^{227}$Th.

3. The compound according to claim 1, wherein the compound is complexed with $^{212}$Pb.

4. A pharmaceutical composition comprising the compound according to claim 2 and a diluent, carrier, surfactant, or excipient.

5. The pharmaceutical composition according to claim 4, further comprising $^{224}$Ra.

6. The pharmaceutical composition according to claim 5, wherein the amount of $^{224}$Ra and $^{212}$Pb is in radioactive equilibrium.

7. The pharmaceutical composition according to claim 6, wherein the activity ratio (MBq) between $^{212}$Pb to $^{224}$Ra is between 0.5 and 2.

8. The pharmaceutical composition according to claim 4, wherein composition is dosaged with a radioactivity of 100 kBq to 100 MBq per dose.

9. The pharmaceutical composition according to claim 4, which is comprised in a kit.

10. A method of inhibiting a cancer comprising administering a pharmaceutical composition according to claim 4 to an individual in need thereof.

11. The method of claim 10, wherein the cancer is prostate cancer.

12. The method of claim 10, wherein the cancer is selected from the group consisting of skeletal metastases from cancers to the breast, prostate, kidneys, lung, bone, and multiple myeloma.

13. The method according to claim 12, wherein the pharmaceutical composition is administered at a dose in the range 50-150 kBq per kg of bodyweight.

* * * * *